United States Patent
Lim et al.

(10) Patent No.: US 12,377,182 B2
(45) Date of Patent: Aug. 5, 2025

(54) STERILIZATION SYSTEM COMPRISING INDEPENDENT PUMP MODULE AND STERILIZATION METHOD THEREOF

(71) Applicant: PLASMAPP CO., LTD., Daejeon (KR)

(72) Inventors: Youbong Lim, Daejeon (KR); Seunghun Lee, Seoul (KR); Jungik Ko, Gyeongsangbuk-do (KR); Junyoung Kim, Hwaseong-si (KR)

(73) Assignee: PLASMAPP CO., LTD., Daejeon (KR)

( * ) Notice: Subject to any disclaimer, the term of this patent is extended or adjusted under 35 U.S.C. 154(b) by 944 days.

(21) Appl. No.: 17/519,769

(22) Filed: Nov. 5, 2021

(65) Prior Publication Data
US 2022/0054679 A1 Feb. 24, 2022

Related U.S. Application Data

(63) Continuation of application No. 17/043,542, filed as application No. PCT/KR2019/015384 on Nov. 13, 2019, now Pat. No. 11,191,860.

(30) Foreign Application Priority Data

| | | |
|---|---|---|
| Jan. 25, 2019 | (KR) | 10-2019-0010100 |
| Jun. 19, 2019 | (KR) | 10-2019-0072837 |
| Nov. 12, 2019 | (KR) | 10-2019-0144259 |

(51) Int. Cl.
*A61L 2/20* (2006.01)
*A61L 2/14* (2006.01)
*A61L 2/26* (2006.01)

(52) U.S. Cl.
CPC ............ *A61L 2/208* (2013.01); *A61L 2/26* (2013.01); *A61L 2/14* (2013.01); *A61L 2202/122* (2013.01); *A61L 2202/24* (2013.01)

(58) Field of Classification Search
CPC .............. A61L 2/208; A61L 2/26; A61L 2/14
See application file for complete search history.

(56) References Cited

U.S. PATENT DOCUMENTS

2005/0147527 A1* 7/2005 Brown ............... A61L 2/208
422/292
2011/0176959 A1 7/2011 Ko
(Continued)

FOREIGN PATENT DOCUMENTS

| CN | 103917250 A | 7/2014 |
|---|---|---|
| CN | 109069678 A | 12/2018 |

(Continued)

OTHER PUBLICATIONS

Communication dated Feb. 25, 2021, from the Korean Intellectual Property Office in application No. 10-2019-0072837.
(Continued)

*Primary Examiner* — Sean E Conley
(74) *Attorney, Agent, or Firm* — Sughrue Mion, PLLC

(57) ABSTRACT

A sterilization system comprises a chamber module and an independent pump module that is external to the chamber module in an independent form, is connected to the chamber module, and has a built-in pump, wherein the chamber module comprises a chamber built in the chamber module and storing a target object and a vaporizer built in the chamber module and connected to the chamber to supply a vaporized sterilant, wherein the chamber built in the chamber module is connected to the pump built in the independent pump module and exhausted.

17 Claims, 21 Drawing Sheets

(56) References Cited

U.S. PATENT DOCUMENTS

| | | | |
|---|---|---|---|
| 2013/0052078 | A1 | 2/2013 | Shilderman et al. |
| 2018/0289846 | A1 | 10/2018 | Cookson et al. |
| 2019/0001008 | A1 | 1/2019 | Lim et al. |
| 2021/0052753 | A1 | 2/2021 | Novotny |

FOREIGN PATENT DOCUMENTS

| | | | |
|---|---|---|---|
| JP | 2004130082 | A | 4/2004 |
| JP | 2011235153 | A | 11/2011 |
| JP | 5214717 | B2 | 6/2013 |
| KR | 20030085689 | A | 11/2003 |
| KR | 101671208 | B1 | 11/2016 |
| KR | 10-2018-0006867 | A | 1/2018 |
| KR | 10-2018-0014809 | A | 2/2018 |
| KR | 1020180015053 | A | 2/2018 |
| KR | 10-2018-0061014 | A | 6/2018 |
| KR | 10-2018-0062989 | A | 6/2018 |
| WO | 2018012690 | A1 | 1/2018 |

OTHER PUBLICATIONS

Communication dated Feb. 9, 2021, from the China National Intellectual Property Administration in application No. 201980023357.2.

Communication dated Apr. 13, 2021, from the Japanese Patent Office in application No. 2020553637.

KIPO Office Action for Application No. 10-2019-0010100 dated Feb. 27, 2019 [Notification for Reason for Refusal].

KIPO Office Action for Application No. 10-2019-0010100 dated Jul. 31, 2019 [Grant for Patent].

International Search Report for PCT/KR2019/015384 dated Feb. 20, 2020 [PCT/ISA/210].

Notice of Allowance issued in parent U.S. Appl. No. 17/043,542 mailed Aug. 4, 2021.

Final Office Action issued in parent U.S. Appl. No. 17/043,542 mailed May 17, 2021.

Office Action issued in parent U.S. Appl. No. 17/043,542 mailed Feb. 1, 2021.

* cited by examiner

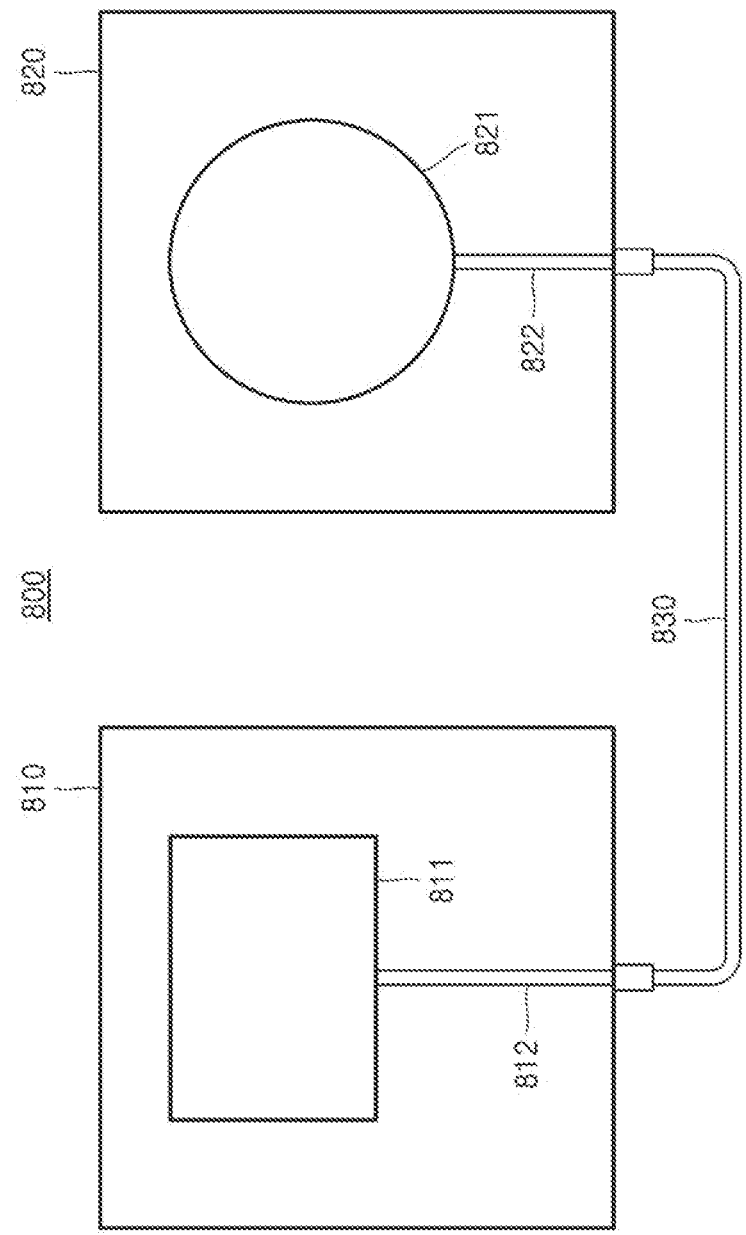

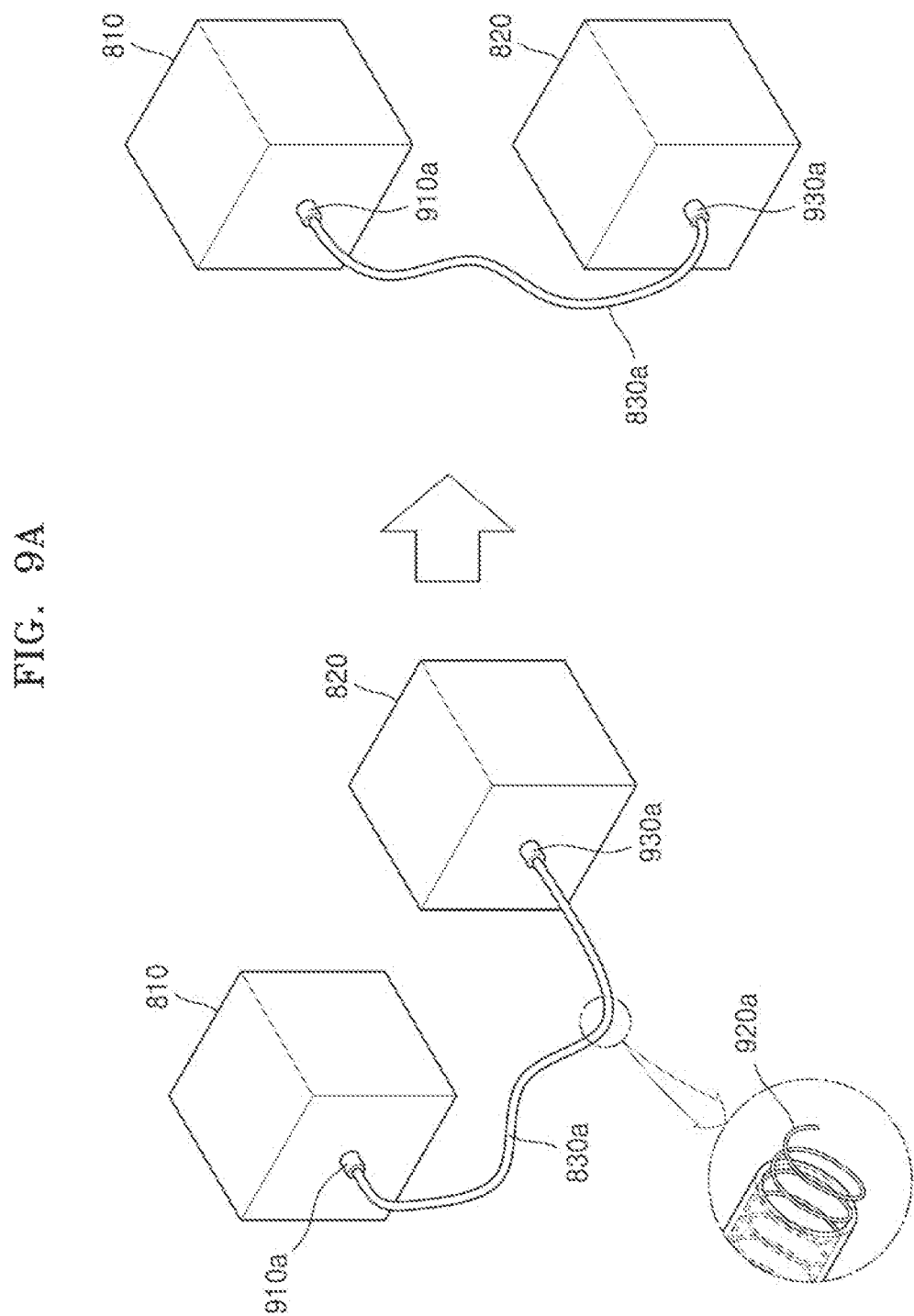

STERILIZATION SYSTEM COMPRISING INDEPENDENT PUMP MODULE AND STERILIZATION METHOD THEREOF

CROSS REFERENCE TO RELATED APPLICATIONS

This application is a continuation of U.S. application Ser. No. 17/043,542 filed on Sep. 29, 2020, which is a National Stage of International Application No. PCT/KR2019/015384, filed on Nov. 13, 2019, which claims priority from Korean Patent Application No. 10-2019-0010100, filed on Jan. 25, 2019, Korean Patent Application No. 10-2019-0072837, filed on Jun. 19, 2019, and Korean Patent Application No. 10-2019-0144259, filed on Nov. 12, 2019.

TECHNICAL FIELD

The present disclosure relates to a sterilization system including an independent pump module and a sterilization method thereof and, more specifically, to a sterilization system and a sterilization method thereof, wherein an independent pump module may be configured to be connected to multiple chamber modules according to a required sterilization capacity.

BACKGROUND ART

Reusable medical devices, such as various surgical instruments, endoscopes, etc., and treatment/procedure tools need to be sterilized prior to reuse as they cause infection when reused in a contaminated state. To this end, various sterilization techniques have been developed, such as gas sterilization with or without steam, hydrogen peroxide, peracetic acid, gas plasma, and ethylene oxide. In particular, a chemical sterilizer performs a sterilization process at low temperature using gases such as hydrogen peroxide ($H_2O_2$), ethylene oxide ($C_2H_4O$) and chlorine dioxide ($ClO_2$) as a sterilant.

DESCRIPTION OF EMBODIMENTS

Technical Problem

Provided is a technology that allows, as one pump module is connected to several chamber modules including a sterilization chamber, a sterilant injection block, and a vaporizer through an independent pump module, exhaust required by each of the chamber modules to be smoothly integrated and efficiently operated.

In addition, provided are a sterilization system and a sterilization method thereof with improved problems such as low space efficiency when operating multiple sterilizers because the size (volume, area, etc.) occupied by a sterilizer is large, and requiring a separate space and facilities because each sterilizer is an independent finished product.

In addition, provided is a technology capable of improving performance or securing the efficiency of product use when using a plurality of chamber modules by using a pump module including a plurality of pumps or a plurality of pump modules.

In addition, provided is a technology capable of maximizing the efficiency of product use when operating only some chamber modules or operating multiple chamber modules at the same time by configuring a plurality of pump modules or a plurality of pumps inside one pump module to effectively operate a plurality of chamber modules.

In addition, provided is a technology in which a pump and a chamber are independently arranged but the arrangement may be changed, and the effective pumping speed of the pump is adjusted by changing a distance between the pump and the chamber, so that the speed and reliability of a sterilization process do not change according to the change of arrangement.

In addition, provided are a sterilization device and a sterilization system capable of additionally connecting an additional chamber module configured independently to a structure in which a basic chamber module and a pump module are combined.

Solution to Problem

According to an aspect of an embodiment, a sterilization system may comprise a chamber module and an independent pump module that is external to the chamber module in an independent form, is connected to the chamber module, and has a built-in pump, wherein the chamber module comprises a chamber built in the chamber module and storing a target object and a vaporizer built in the chamber module and connected to the chamber to supply a vaporized sterilant, wherein the chamber built in the chamber module is connected to the pump built in the independent pump module and exhausted.

In some embodiments, the chamber may include an impermeable wrapper in which the target object is stored, the vaporizer is connected to the impermeable wrapper to supply air or a sterilant, and the impermeable wrapper is connected to the independent pump module to exhaust air from the impermeable wrapper.

In some embodiments, the volume of the impermeable wrapper may be controlled by exhausting air in the chamber by the independent pump module.

In some embodiments, an exhaust port through which air of the chamber module is exhausted or an inlet port of the independent pump module may be connected to a plasma source or a catalyst.

In some embodiments, after the volume of the impermeable wrapper is expanded, the sterilant may be vaporized through the vaporizer and injected into the impermeable wrapper, the impermeable wrapper is exhausted through the independent pump module to exhaust the sterilant, and the chamber and the impermeable wrapper are vented to atmospheric pressure.

In some embodiments, the independent pump module may be connected to the second chamber module to exhaust air of the second chamber module.

In some embodiments, the independent pump module may be connected to the chamber module and the second chamber module through a diverging tube.

In some embodiments, the diverging tube or an exhaust line included in the chamber module may include a backflow prevention module.

In some embodiments, the independent pump module may include a plurality of pumps, and each of the plurality of pumps is connected to a tube including a valve.

In some embodiments, the chamber module may have a combining structure on an upper surface or a side surface, and is combined with a combining structure on a lower surface or a side surface of the second chamber module, or is combined with a combining structure on a lower surface or a side surface of the independent pump module and fixed.

In some embodiments, the chamber module may obtain information about a sterilization process of the chamber module and information about a sterilization process of the second chamber module, and controls exhaust through the independent pump module to occur in at least one of the chamber module or the second chamber module.

In some embodiments, the chamber module may allow exhaust through the independent pump module to occur only in a target pump module by closing or opening a valve provided in at least one of the diverging tube, an exhaust port of the chamber module, and an exhaust port of the second chamber module.

In some embodiments, the information about the sterilization process may include information about the size or the amount of remaining moisture of the target object, and the chamber module derives an order and time required for the sterilization process of the chamber module, and an order and time required for the sterilization process of the second chamber module.

In some embodiments, the chamber module may delay one of the sterilization processes of the chamber module and the second chamber module to synchronize the sterilization process of the chamber module with the sterilization process of the second chamber module.

In some embodiments, the sterilization system may further comprise a control module to control exhaust through the independent pump module to be performed in at least one of the chamber module and the second chamber module by obtaining information about a sterilization process of the chamber module and information about a sterilization process of the second chamber module.

According to an aspect of an embodiment, a sterilization pump assembly includes: a pump configured to exhaust air inside a chamber in which a sterilization process of a target object is performed; and a connector, through which internal air flows, configured to connect the pump to the chamber, so that the arrangement of the pump may be changed independently.

In some embodiments, the sterilization pump assembly may further include a housing having a combiner to which the connector is combined, and surrounding the outside of the pump.

In some embodiments, a connection point of the chamber and the connector, a connection point of the pump and the connector, and a length of the connector are fixed, and the arrangement of the pump and the connector may change by rotating the connector.

In some embodiments, a connection point of the chamber and the connector and a connection point of the pump and the connector are fixed, and the arrangement of the pump and the connector may change by rotating the connector or adjusting a length of the connector.

In some embodiments, a length of the connector may be within 1.5 m.

In some embodiments, the sterilization pump assembly may further include a controller configured to control operations of the pump by using information related to the length of the connector.

In some embodiments, the sterilization pump assembly may further include a controller configured to control the operation intensity or time of the pump, wherein the controller may determine suitability of the arrangement according to the connection unit through a test run mode in which the pump is operated with a reference value, or may adjust a value for controlling the pump in an operation mode other than the test run mode.

In some embodiments, the connector may include a backflow prevention module to prevent the internal air from flowing into the chamber.

In some embodiments, the connector may be made of a flexible material, but may include a material having chemical resistance inside a path through which the internal air flows, to prevent damage by a material contained in the internal air.

In some embodiments, the connector may include a hard material outside the path through which the internal air flows, to prevent damage or deformation due to external physical impact.

In some embodiments, the housing may further include a fan to exhaust air inside the housing to the outside of the housing.

According to another aspect of an embodiment, a sterilization chamber assembly includes: a chamber in which a sterilant is supplied to sterilize a target object stored therein, and internal air is exhausted by a pump; and a connector, through which the internal air flows, configured to connect the pump to the chamber, so that the arrangement of the chamber may be changed independently.

In some embodiments, the sterilization chamber assembly may further include a filter arranged in a path for exhausting the internal air to the outside of the chamber.

In some embodiments, the sterilization chamber assembly may further include: a sterilant container in which the sterilant is stored; and a vaporizer configured to receive the sterilant from the sterilant container, and heat the sterilant, vaporize the sterilant, and supply the sterilant to the chamber.

According to another aspect of an embodiment, a sterilization system includes: a chamber in which a sterilant is supplied to sterilize a target object stored therein; a pump configured to exhaust internal air of the chamber; and a connector, through which the internal air flows, configured to connect the pump to the chamber, so that the arrangement of the pump may be changed independently.

In some embodiments, the sterilization system may further include: a pump housing having a pump-connector combiner to which the connector is combined, and surrounding the outside of the pump; and a chamber housing having a chamber-connector combiner to which the connector is combined, and surrounding the outside of the chamber.

In some embodiments, the pump housing may further include a fan to exhaust air in the housing to the outside.

In some embodiments, the sterilization system may further include: a power unit configured to supply power to drive pump operations of the pump or sterilization operations of the chamber; and a power line configured to connect the pump to the chamber independently so that the arrangement may be changed.

According to another aspect of an embodiment, a sterilization device includes: a basic chamber module; and a pump module that is combined with the basic chamber module and has a built-in pump, wherein the pump module may include: a first combiner for connecting the basic chamber module to the pump; and a second combiner for connecting at least one additional chamber module to the pump, the at least one additional chamber module being configured to be independent from the sterilization device and connected to the pump module.

In some embodiments, the pump module may include: a first inner tube connected between the built-in pump and the first combiner to circulate internal air; and a second inner tube connecting the built-in pump to the second combiner.

In some embodiments, the pump module may include a plurality of second combiners to connect the pump to each of at least two additional chamber modules.

In some embodiments, the second inner tube may diverge to correspond to the number of the plurality of second combiners in order to connect each of the plurality of second combiners to the pump.

In some embodiments, the first inner tube and the second inner tube may be gathered into one third inner tube and connected to the pump.

In some embodiments, the at least one additional chamber module may be connected to the second combiner through at least one outer tube.

In some embodiments, the at least one additional chamber module may include: a chamber configured to store a target object; and a vaporizer connected to the chamber to supply a vaporized sterilant.

In some embodiments, the sterilization device may further include: a processor configured to detect the number of one or more additional chamber modules connected to each other through the second combiner and to control a pumping speed, a pumping intensity, or a pumping time of the pump according to the detected number of the additional chamber modules.

In some embodiments, the processor may be built in the pump module.

According to another aspect of an embodiment, a sterilization device includes: a basic chamber module; and a pump module combined with the basic chamber module and having a built-in pump, wherein the basic chamber module may include: a first combiner for connecting the pump module to the basic chamber module; a second combiner for connecting the basic chamber module to an additional chamber module detachable from the basic chamber module in an independent form; and an inner tube connected between the first combiner and the second combiner to circulate internal air.

In some embodiments, the inner tube, in order to circulate internal air between a chamber in the basic chamber module and the pump module, may diverge toward the chamber in a path between the first combiner and the second combiner.

In some embodiments, the basic chamber module may further include a vaporizer between the chamber and the first combiner.

In some embodiments, the sterilization device may further include: a processor configured to detect the number of connected additional chamber modules and to control a pumping speed, a pumping intensity, or a pumping time of the pump according to the detected number of the additional chamber modules.

In some embodiments, the additional chamber module may be combined with the basic chamber module in a form of being stacked on top of the basic chamber module.

According to another aspect of an embodiment, a sterilization system includes: a basic chamber module; a sterilization device that is combined with the basic chamber module and includes a pump module having a built-in pump; and at least one additional chamber module configured in a form independent from the sterilization device and detachable from the pump module or the basic chamber module.

Advantageous Effects of Disclosure

According to a method and an device according to an embodiment, by configuring a chamber module including a sterilization chamber without a vacuum pump and configuring the vacuum pump as an independent module, the area occupied by the entire facility is reduced when a plurality of chamber modules are connected to each other and used.

In addition, because an independent pump module has an operation schedule in a process of exhausting air to a plurality of chamber modules, each chamber module may have the same level of operating time and performance as constituting a pump module therein.

Also, as each chamber module is configured to selectively operate sterilization operations through a chamber and sterilization operations through a pouch, there are no restrictions on the size and type of objects to be sterilized, and if necessary, it is possible to prevent secondary contamination by vacuum sealing after sterilization is completed.

In addition, the independent pump module may selectively and repeatedly perform injection and exhaust of air for each chamber module, so that the volume area of a target object may be calculated or the amount of remaining moisture may be checked.

In addition, the independent pump module is configured to operate even in a process of exhausting a sterilant from each chamber module so that all remaining sterilant may escape and at the same time, the corresponding sterilant removes contaminants contained in waste through subsequent treatment.

In addition, a sterilization system according to the present disclosure may be used in various industrial fields using instruments including beauty industry, such as beauty and nail art, in addition to the medical industry.

An assembly and a system according to an embodiment have an effect of improving space efficiency by changing the arrangement of a sterilization device in a space.

In addition, the assembly and system according to an embodiment have an effect of increasing sterilization efficiency by disposing a chamber and a pump as separate spaces.

In addition, the assembly and system according to an embodiment have an effect that the speed and reliability of a sterilization process do not change according to the change of the arrangement by adjusting the effective pumping speed of a pump as the arrangement of the assembly and system is changed.

In addition, a device and a method according to an embodiment have an advantage that an additional chamber module that is independently configured may be additionally connected to a structure in which a basic chamber module and a pump module are combined, according to a situation.

BRIEF DESCRIPTION OF DRAWINGS

The above and other aspects, features, and advantages of certain embodiments of the present disclosure will be more apparent from the following description taken in conjunction with the accompanying drawings, in which:

FIGS. 2A and 2B are views of a chamber module as an example according to the present disclosure, wherein FIG. 2A is a front view of the chamber module, and FIG. 2B is a rear view of the chamber module.

FIGS. 3A and 3B are views of an independent pump module as an example according to the present disclosure, wherein FIG. 3A is a front view of the independent pump module, and FIG. 3B is a rear view of the independent pump module.

FIG. 8 is a block diagram of a sterilization system according to an embodiment;

FIGS. 9A to 9C are views for explaining a change in an arrangement between a chamber and a pump in a sterilization system according to an embodiment;

BEST MODE

Figure 1:
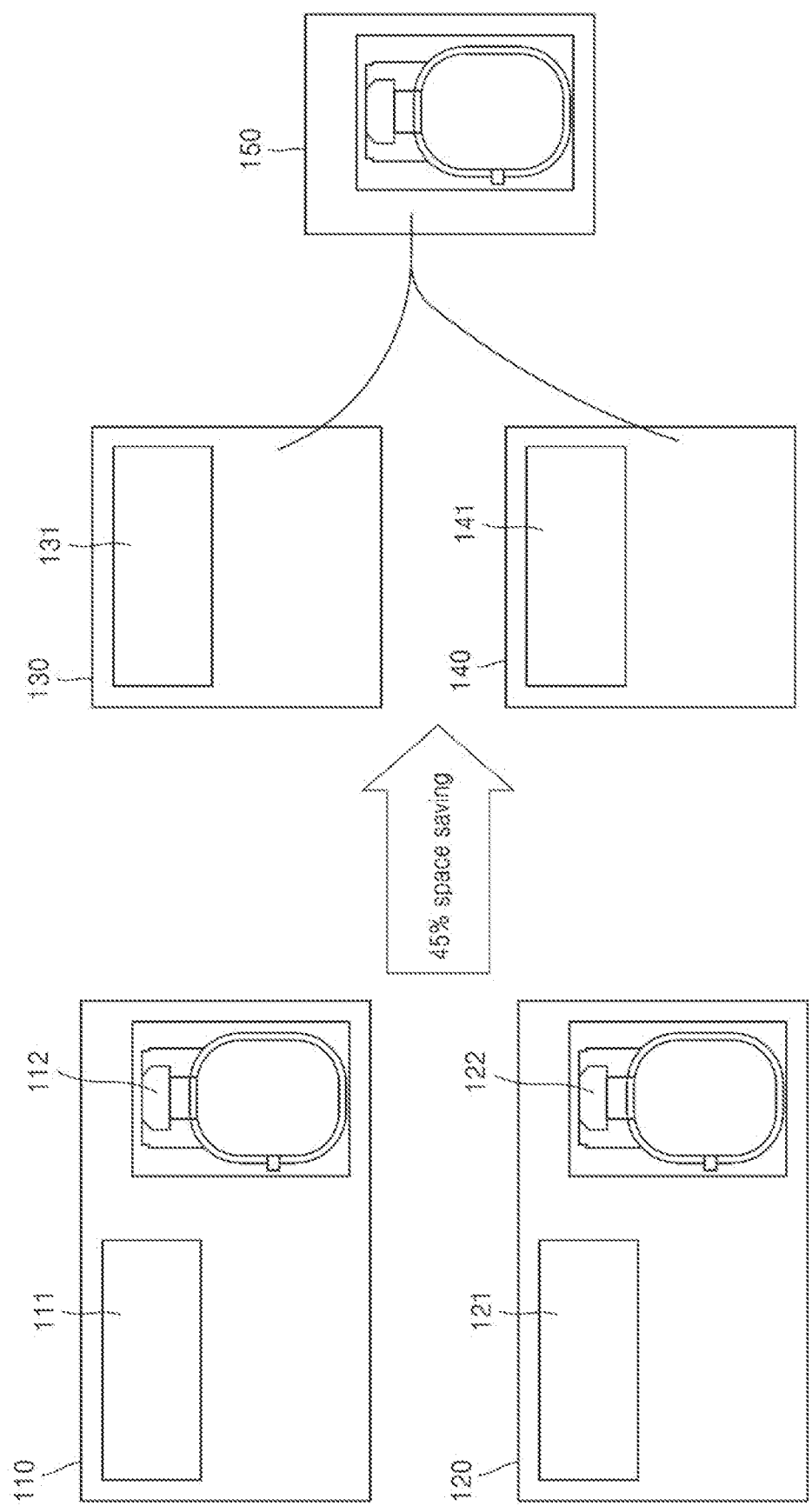
FIG. 1 is a view illustrating an effect of reducing the size of a device compared to a conventional sterilization device provided with several, through an example according to the present disclosure.

The present disclosure provides a sterilization system including an independent pump module connected to a plurality of chamber modules to exhaust air from each of the chamber modules, in particular, a technique for performing exhaust air required in each chamber module by an external independent pump module.

Each chamber module is equipped with a device configuration that stores an object to be sterilized and sterilizes the object by reacting with a sterilant. In this case, the chamber module may include both a form in which a target object is stored in a chamber and a form in which a target object is stored in an impermeable sealed container.

The impermeable sealed container may be used synonymously with "pouch" used in a sterilizer technology, and may be referred to as "impermeable wrapper" to indicate the constitutive contents for sterilization of a target object.

The present disclosure is a technology that can be applied to a sterilization device employing a variety of sterilization methods that are not restricted by its shape and mechanism. The following embodiments are disclosed in a manner applied to a medical low-temperature plasma sterilizer that performs a sterilization process of an object to be sterilized by using hydrogen peroxide as a sterilant.

According to the above object, the present disclosure will be described in more detail.

In a sterilization process, it is common to perform chemical sterilization in which hydrogen peroxide is vaporized and exposed to a target object to inactivate microorganisms through oxidation reactions of cell walls and nuclei of the microorganisms remaining in the target object.

In addition, the medical low-temperature plasma sterilizer uses plasma to secure user safety by purifying a sterilant. The plasma is a material in a fourth state defined as a quasi-neutral gas due to its electrical characteristics, and may be formed by applying electrical energy. In particular, high voltage power is applied to a cracking plasma source (CPS) to generate plasma at atmospheric pressure, and a sterilant (hydrogen peroxide, $H_2O_2$) exhausted after the sterilization process is decomposed and purified into water ($H_2O$) and oxygen ($O_2$) through plasma treatment.

A sterilization system according to an embodiment is a device or a plurality of connected devices in which a sterilant is supplied to a chamber in which an object to be sterilized (target object) is stored to perform a sterilization process for the object in the chamber, and the air inside the chamber may be exhausted by a pump during the sterilization process, before the sterilization process, or after the sterilization process.

A sterilization system according to an embodiment is a chemical sterilizer that performs a sterilization process at a low temperature by using a gas such as hydrogen peroxide ($H_2O_2$), ethylene oxide ($C_2H_4O$), and chlorine dioxide ($ClO_2$) as a sterilant.

In a sterilization system according to an embodiment, a chamber in which a sterilization process is performed and a pump for exhausting air inside the chamber are independently arranged, and this arrangement is configured to be changeable, and thus the sterilization system may achieve high space efficiency according to various arrangement types. Also, as the chamber and the pump are arranged independently of each other, the chamber in which the sterilization process is performed is less affected by contaminants (e.g., oil for hydraulic pumps), noise, and vibration caused by the pump, thereby increasing the reliability and efficiency of the sterilization process.

According to an embodiment, the sterilization system is configured to vaporize a sterilant required in the sterilization process. In this case, the sterilization system may reduce temperature reduction due to air discharged through the pump or a configuration (e.g., a fan) for discharging the air to the outside of a device by including a vaporizing component on the chamber side.

According to an embodiment, the sterilization system may adjust a distance to a connector through which exhaust air flows between the chamber and the pump. At this time, the sterilization system may adjust effective pumping speed that changes as the distance increases by adjusting operating time and intensity of the pump based on information related to the distance, so that the speed and reliability of the sterilization process performed in the chamber do not change.

FIG. 1 is a view illustrating an effect of reducing the size of a device compared to a conventional sterilization device provided with several, through an example according to the present disclosure.

Referring to FIG. 1, as shown in the left side of the drawing, in the case of operating a plurality of sterilization devices, each of devices 110 and 120 needs to have both sterilization chambers 111 and 121 and vacuum pumps 112 and 122.

However, in the case of configuring to operate two sterilization chambers through an example according to the present disclosure (as shown on the right side of the drawing), because a first chamber module 130 including a first sterilization chamber 131 and a second chamber module 140 including a second sterilization chamber 141 are connected to an independent pump module 150, the area occupied by the entire system is reduced.

However, this effect is large when a plurality of chamber modules are connected to one independent pump module among various embodiments.

Figure 2A:
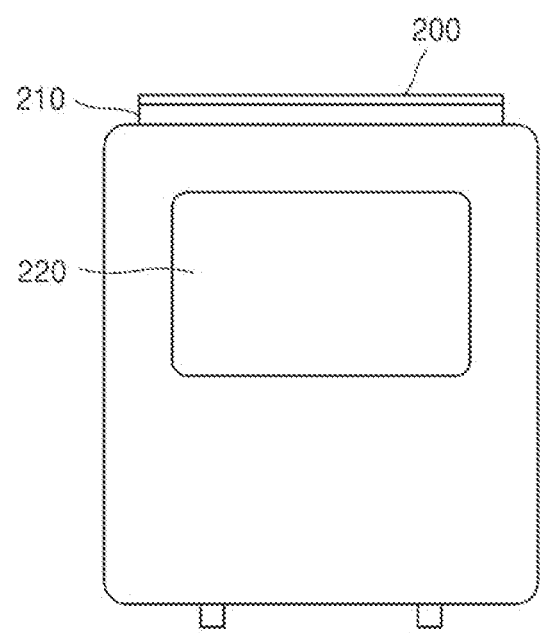
Figure 2B:
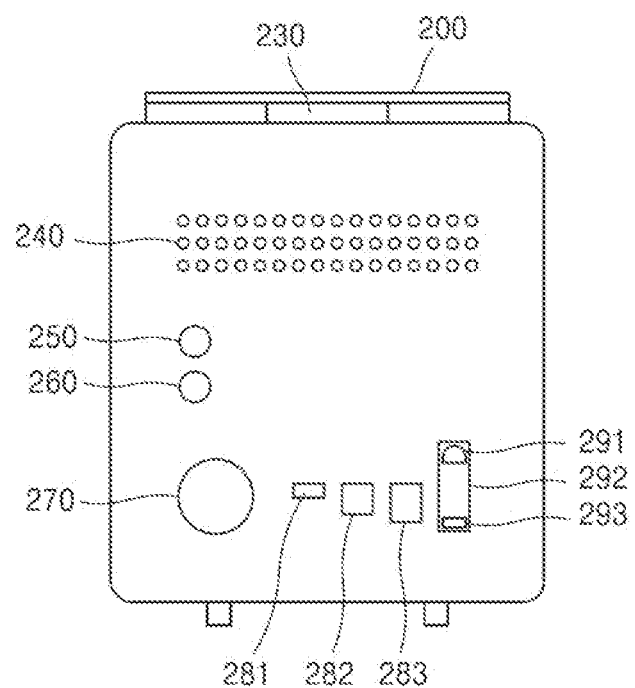
Figure 3A:
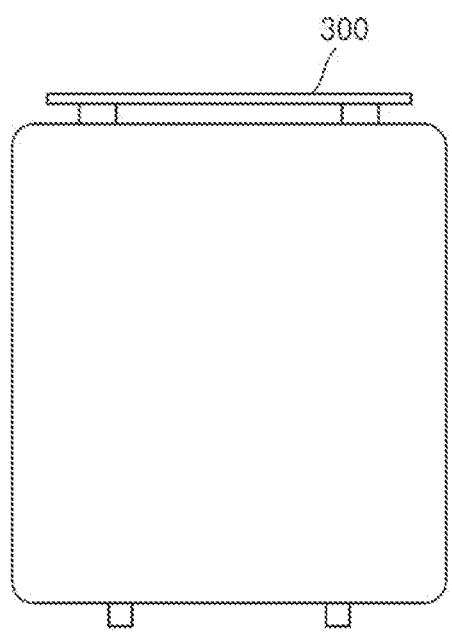
Figure 3B:
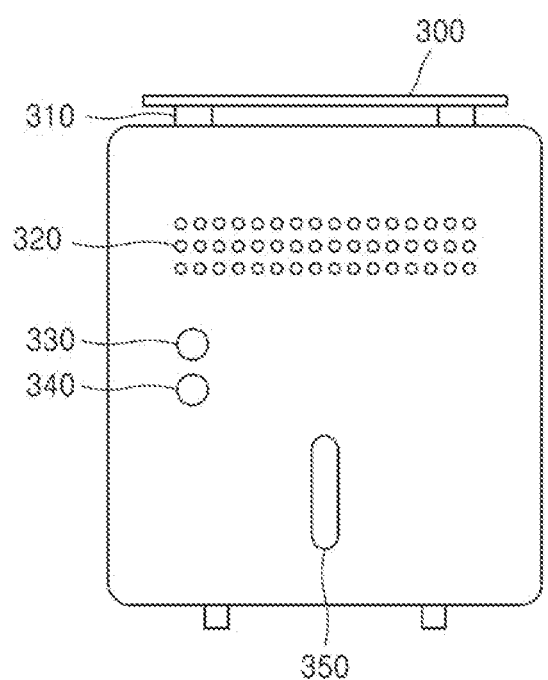
Figure 4:
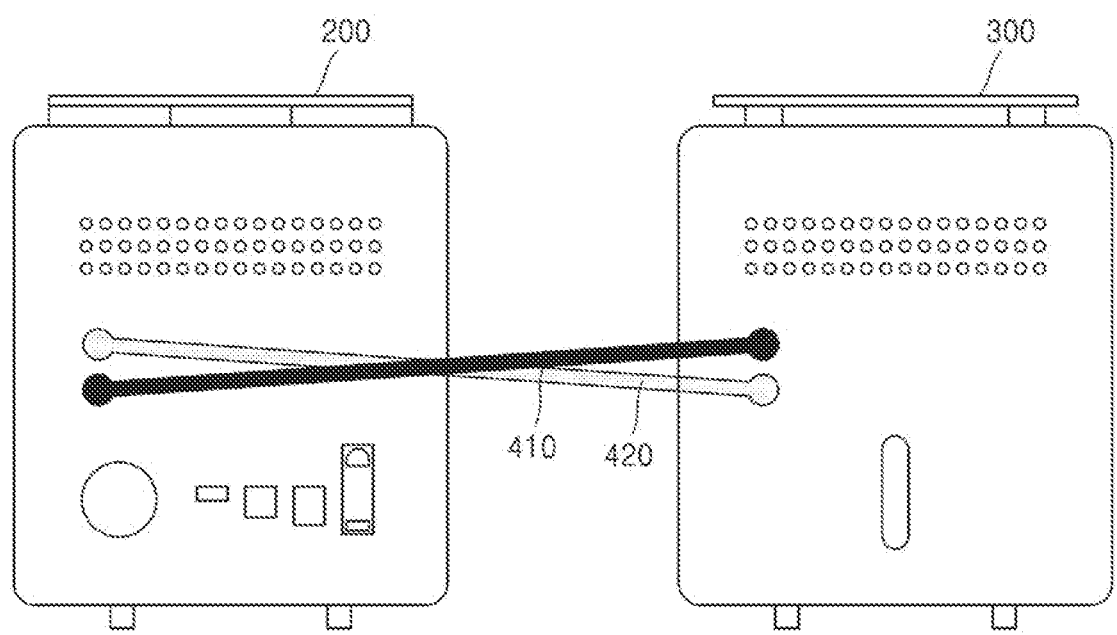
FIG. 4 is a view illustrating a state in which a chamber module and an independent pump module are connected to each other, as an example according to the present disclosure.

FIGS. 2A and 2B are views of a chamber module as an example according to the present disclosure, wherein FIG. 2A is a front view of the chamber module, and FIG. 2B is a rear view of the chamber module. FIGS. 3A and 3B of an independent pump module as an example according to the present disclosure, wherein FIG. 3A is a front view of the independent pump module, and FIG. 3B is a rear view of the independent pump module. FIG. 4 is a view illustrating a state in which a chamber module and an independent pump module are connected to each other, as an example according to the present disclosure.

Referring to FIGS. 2 to 4, an independent pump module 300 is connected to a chamber module 200 to exhaust air from a chamber module 200.

The chamber module 200 includes a door cover 210 and a touch screen 220 on the front side, and includes a door hinge 230, a ventilation hole 240, a pump connector 250, a power line connector 260, a filter 270, a plurality of universal serial bus (USB) ports 281 and 282, a LAN cable port 283, a power connection terminal 291, a fuse cap 292, and a power switch 293 on the rear side.

The door cover 210 includes an upper cover of the chamber module 200 and may be opened and closed using the door hinge 230. According to an embodiment, a container (e.g., chamber) may be exposed to the outside of a device such that an object to be sterilized may be stored in the chamber module 200 through the door cover 210.

The touch screen 220 is a touch panel that receives a user input for operating a module, and enables product status and history management. According to an embodiment, the touch screen 220 externally displays a sterilization process of the chamber module 200, the time required for the sterilization process, whether the sterilization process is possible, and an error occurring during the sterilization process.

The door hinge 230 may be connected to the door cover 210 such that the door cover 210 of the chamber module 200 may be opened and closed.

The ventilation hole 240 may be a plurality of holes for ventilation arranged in a stripe shape such that the exhaust by a fan is smoothly made and air is introduced.

The pump connector 250 is connected to the independent pump module 300 through a pneumatic tube, and is fitted such that the flow of air operates accurately. The pump connector 250 has a diverging point in the chamber module 200 such that air is exhausted to each of the chamber and an impermeable wrapper, and may have a valve configuration to enable individual exhaust according to an embodiment.

For example, pressure may be controlled by exhausting the independent pump module 300 and selectively exhausting the chamber or the impermeable wrapper through opening or closing of the valve additionally configured in the pump connector 250.

The power line connector 260 is a connector to which a power line for supplying power to the independent pump module 300 is connected.

According to an embodiment, when a plurality of chamber modules are configured in a sterilization system, power may be directly supplied to only one of the plurality of chamber modules. In this case, the power line may be connected to one of the plurality of chamber modules, and power may be supplied to the other chamber module and the independent pump module through the one chamber module to which the power line is connected. For example, a chamber module may be designed by being divided into a main chamber module receiving power directly and a secondary chamber module receiving power through the main chamber module.

The filter 270 is a replaceable filter for blocking dust or microorganisms in the air in the process of forming and venting a vacuum. During a sterilization process, exhaust by the independent pump module is the exhaust of the air inside the chamber and the impermeable wrapper, so when air is required to be introduced into the chamber and the impermeable wrapper, a connecting valve for exhausting is closed and a connecting valve for venting is opened to allow external air to be introduced. At this time, because a sterilization effect or sterilization reliability may be lowered by contaminants contained in the supplied air, the filter 270 may be provided on the side of a path through which external air flows.

USB ports 281 and 282 may include the first USB port 281 for software update and the second USB port 282 for communicating with a printer for outputting a sterilization log. According to an embodiment, the main chamber module may support software update or output of related information for other secondary chamber modules and independent pump modules that are connected to the main chamber module with such a port configuration.

The LAN cable port 283 is a port that transmits device status information to a server and connects the device to the Internet to enable remote control of the device. According to an embodiment, the LAN cable port 283 performs a device-like function for data connection with an external control module (e.g., a computing device with a management program). According to an embodiment, the LAN cable port 283 may be replaced with a device-like configuration through wireless communication connection such as WiFi and Bluetooth, including wired connection through a LAN line.

The power connection terminal 291 is a connection terminal for supplying electricity to the chamber module 200.

A fuse cap 292 is installed for simple replacement of a fuse connected to a main power supply of a product.

The power switch 293 is a switch for turning on/off the power of the chamber module 200.

The independent pump module 300 includes a cover 310 on the front side, and includes a ventilation hole 320, a power connector 330, a pump connector 340, and a pump oil status display unit 350 on the rear side.

The cover 310 has a shape designed to express an appearance similar to that of the chamber module 200.

The ventilation hole 320 may be a plurality of holes for ventilation arranged in a stripe shape such that the exhaust by a fan is smoothly made and air is introduced.

The power connector 330 is a connector that receives power by being connected to the power line connector 260 of one chamber module 200 through a power line cable 410.

The pump connector 340 is connected to a plurality of chamber modules 200 through a pneumatic tube 420 to allow air to flow so that air is exhausted from each of the chamber modules 200, and is fitted to accurately flow air.

The pump oil status display unit 350 is formed to check the amount and state of oil in an oil rotary pump.

For example, the pump oil status display unit 350 is made of a light-transmitting material, and is configured to be in contact with an internal oil container of the independent pump module 300 to check how full the internal oil is and the color of the internal oil from the outside of the pump module 300.

Figure 5:
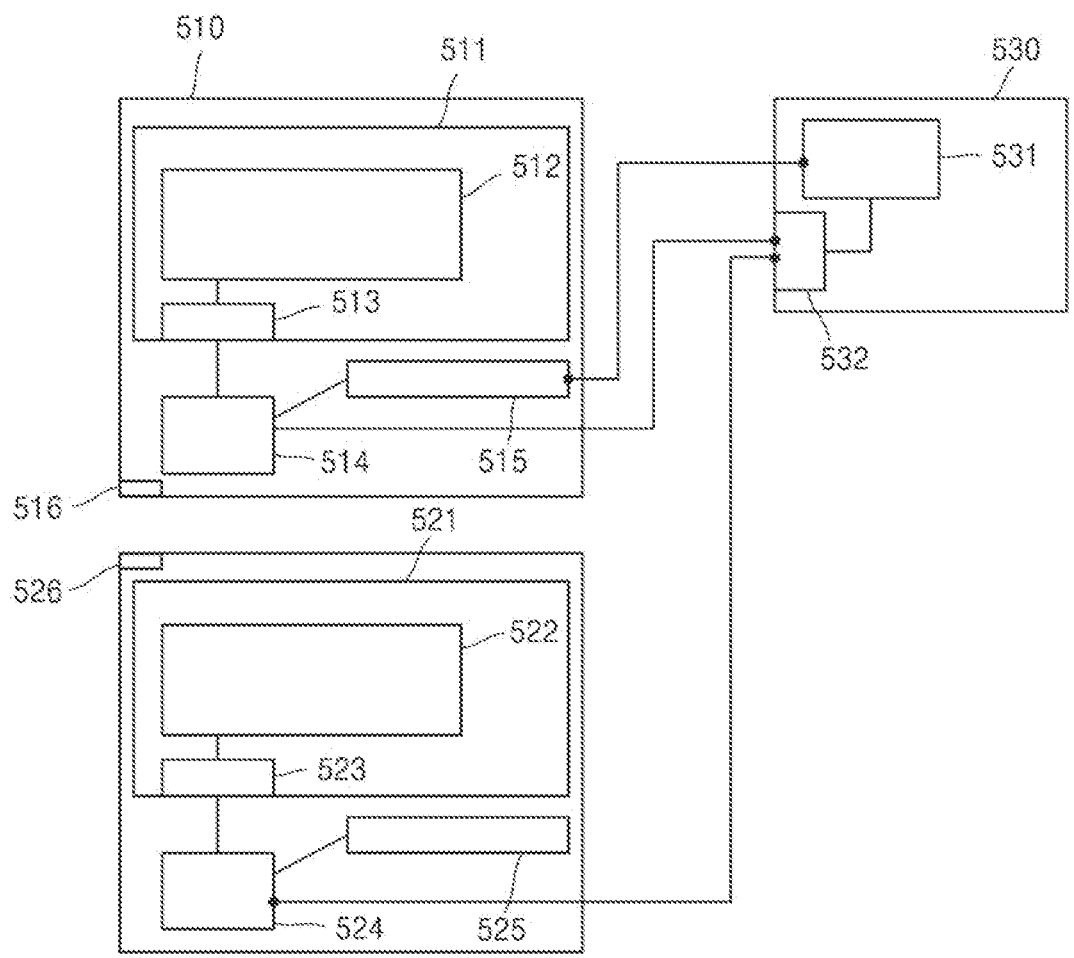
FIG. 5 is a schematic view of a sterilization system, as another example according to the present disclosure.

FIG. 5 is a schematic view of a sterilization system, as another example according to the present disclosure.

Referring to FIG. 5, another example sterilization system according to the present disclosure includes a first chamber module 510, a second chamber module 520, and an independent pump module 530.

The independent pump module 530 is connected to the plurality of chamber modules 510 and 520 to exhaust air from the chamber modules 510 and 520, respectively.

According to a preferred embodiment, the first chamber module 510 includes a chamber 511 having a wrapper 512 in which a first target object is stored, and the air inside the chamber 511 or the wrapper 512 is exhausted by the independent pump module 530.

In addition, the second chamber module 520 includes a chamber 521 having a wrapper 522 in which a second target object is stored, and the air inside the chamber 521 or the wrapper 522 is exhausted by the independent pump module 530.

According to an embodiment, the wrappers 511 and 522 may be implemented with an impermeable material through which liquid or gas is not permeable.

In this case, the independent pump module 530 may include a module 532 where tubes connected to each other to support exhaust for the first chamber module 510 and the second chamber module 520 diverge.

According to another preferred embodiment, the independent pump module 530 is connected to the first chamber module 510 and the second chamber module 520 through the tubes 541 and 542 through which air flows.

Sterilization using the wrappers 512 and 522 is advantageous for the diffusion and reaction of a sterilant during a sterilization process, and there is an advantage that the a sterilized target object may be wrapped and stored in the wrapper 512 and 522 in order to maintain sterility until is used with high vaporization efficiency of the sterilant.

According to another example of the present disclosure, the first chamber module 510 or the second chamber module 520 may exhaust the air inside the chambers 511 and 521 and the wrappers 512 and 522 through exhaust by the independent pump module 530 during a sterilization process to lower internal pressure, and may stop exhausting of the chambers 511 and 521 and repeat exhausting and venting of the wrappers 512 and 522 to heat a target object stored in the wrappers 512 and 522. Also, according to an embodiment, in this process, the volume and capacity of the target object may be calculated by measuring the time required in the process of exhausting and venting the wrappers 512 and 522 or the time to reach a specific pressure level.

According to another example of the present disclosure, after heating an inner target object through exhaust and venting of the wrappers 512 and 522, the amount of water remaining inside a target object or the wrappers 512 and 522 may be measured by measuring the level at which internal pressure increases by sufficiently exhausting the wrappers 512 and 522 at a prescribed pressure level and venting the wrappers 512 and 522 again.

When volume measurement, heating, and removal of residual moisture for the target object are completed, a sterilant is injected to sterilize the target object stored in the wrappers 512 and 522. In this process, after the chambers 511 and 521 are exhausted through the independent pump module 530 or exhausted to a prescribed pressure level, the wrappers 512 and 522 may be sealed so that the exhaust is not performed.

According to an embodiment, the first chamber module 510 and the second chamber module 520 may perform a sterilization process on a target object stored in the chambers 511 and 521 through a process in which the target object is directly stored in each of the chambers 511 and 521 without the wrappers 512 and 522, and a sterilant is supplied and spread through sterilant injectors 513 and 514, and a process of exhausting the supplied sterilant. That is, the first chamber module 510 and the second chamber module 520 may support the sterilization process through the wrappers 512 and 522 and the sterilization process through the chambers 511 and 521 to be performed by a user's selection considering the size, type, and usage type after sterilization of the target object.

In this case, the independent pump module 530 is configured to be defined in advance or operated according to a command through a controller because the time at which air is exhausted in the sterilization process through the wrappers 512 and 522 and the time at which air is exhausted in the sterilization process through the chambers 511 and 521 are different from each other.

The sterilization process through the chambers 511 and 521 may be performed using a TYVEK® pouch used in general medical low-temperature plasma sterilizers. A sterilant may pass through the TYVEK® film and sterilize a target object inside the TYVEK® film, but because microorganisms cannot pass through the TYVEK® film, aseptic preservation is ensured. In this case, the sterilization process may be achieved by employing and binding a sterilant injector that supplies a suitable sterilant.

In the sterilization process through the wrappers 512 and 522, a needle may be connected to a silicone pad portion of the wrappers 512 and 522 to directly supply a sterilant into the wrappers 512 and 522, and may directly remove the sterilant remaining after the sterilization process. As the needle is removed after the entire process is completed, the wrappers 512 and 522 may be completely sealed in a vacuum state to ensure aseptic preservation.

According to an embodiment, the independent pump module 530 may perform an exhaust operation by receiving an operation command from the first chamber module 510, the second chamber module 520, and an external control module (e.g., a computing device with a management program).

According to an embodiment, the independent pump module 530 may be driven in an exhaust state continuously while a sterilization process of the first chamber module 510 and/or the second chamber module 520 is performed. A connection configuration (e.g., a valve, etc.) diverges to allow exhaust from each of the chambers 511 and 521 and the wrappers 512 and 522 may be provided in the first chamber module 510 and/or the second chamber module 520 where the sterilization process is performed. Exhaust or sealing may be achieved through the connection configuration (e.g., a valve, etc.).

According to another embodiment, the independent pump module 530 may have a connection configuration between the chamber 511 and the wrapper 512 of the first chamber module 510 and between the chamber 521 and the wrapper 522 of the second chamber module 520. The connection configuration includes a valve or the like, and may perform exhaust or sealing of each of the chambers 511 and 521 and the wrappers 512 and 522.

When the independent pump module 530 simultaneously exhausts the first chamber module 510 and the second chamber module 520, because the pressure of the first chamber module 510 and the pressure of the second chamber module 520 are different from each other, air may flow from a higher pressure chamber module to a lower pressure chamber module. In order to prevent this, the independent pump module 530 may configure a backflow prevention module such as a check valve at a side connected to each chamber module in the module 532 where a tube diverges.

According to another embodiment, the first chamber module 510 may have a combining structure 516 on an upper surface, a lower surface, or a side surface. The first chamber module 510 may be combined and fixed with the second chamber module 520 having the combining structure 526, which is combined with the combining structure 516 of the first chamber module 510 and fixed in pairs, on the upper surface, the lower surface, or the side surface.

According to an embodiment, the independent pump module 530 may have a combining structure (not shown) paired with the combining structure of the first chamber module 510 or the second chamber module 520 on the upper surface, the lower surface, or the side surface. In this case, the independent pump module 530 and the first chamber module 510 and/or the second chamber module 520 may be combined with each other to be fixed.

According to an embodiment, the independent pump module 530 is configured in a buried form in a wall or a floor rather than a separate device configuration, so that only connectors such as a tube or a power connection line may exist on the wall or floor.

According to an embodiment, the first chamber module 510 includes an operation controller (not shown), and injection, diffusion, exhaust, and purification of the sterilant are performed through the operation controller.

At this time, the operation controller of the first chamber module 510 may define or control an operation schedule for an exhaust operation of the independent pump module 530 and for which tube is to be connected in the module 532 where the tube diverges upon exhaust.

According to an embodiment, the module 532 where the tube diverges may be configured as a valve and closed or opened so that exhaust through the tube is performed only for a desired chamber module.

According to an embodiment, the module 532 where the tube diverges may be operated to exhaust air from a plurality of tubes, and in this case, the exhaust time or the exhaust intensity may be increased.

According to another embodiment, the operation controller of the first chamber module 510 may receive information requested for all sterilization processes by receiving a target object from the second chamber module 520, and may define or control an operation schedule through this information.

According to an embodiment, the information requested for the sterilization processes may include information about the volume, surface area size, or moisture content of an object to be sterilized.

According to an embodiment, through an initial pumping process of injecting air into the wrappers 512 and 522, the volume or the surface area size of the object may be derived through a relationship between a pressure value of the wrappers 512 and 522 and the time at which air is injected.

According to another embodiment, the operation controller of the first chamber module 510 calculates a time point at which exhausting is required during the sterilization process of the first chamber module 510 and the second chamber module 520 that require a sterilization process, adjusts a time point at which an exhaust process is required in each module, and schedules the earlier time point at which the sterilization process is completed later among the chamber modules 510 and 520.

According to an embodiment, the operation controller may newly define an operation schedule whenever there is a request for a sterilization process in a connected chamber module.

According to an embodiment, the operation controller may be included in the first chamber module 510, the second chamber module 520, or the independent pump module 530, and may be configured as a separate device or may function through a server or an external computer.

According to an embodiment, the operation controller, when sterilization processes are performed at a certain time interval in the first chamber module 510 and the second chamber module 520, may synchronize the sterilization processes performed in the two chamber modules by delaying a specific process for the chamber module in which the sterilization process is performed faster. It is important to have the reliability of the sterilization process as much as the fast sterilization process is performed in each chamber module. This is because, when each chamber module is exhausted by one independent pump module and a different stage of sterilization process is in progress, a desired pressure level cannot be met due to the reverse flow of air, and there is a possibility of malfunction.

According to another embodiment, the first chamber module 510 includes the sterilant injector 513 for injecting a sterilant into the wrapper 512 and the vaporizer 514 for heating and vaporizing the sterilant.

In addition, the second chamber module 520 includes a sterilant injector 523 for injecting a sterilant into the wrapper 522 and a vaporizer 524 for heating and vaporizing the sterilant.

At this time, the independent pump module 530 exhausts the air in the chambers 511 and 521 and increases the volume of the impermeable wrappers 512 and 522, so that the vaporized sterilant may be easily diffused into the impermeable wrappers 512 and 522. This is because the impermeable wrappers 512 and 522 are swollen to provide a space for spreading the sterilant.

According to an embodiment, the vaporizers 514 and 524 may be directly connected to the wrappers 512 and 522 to supply air and a sterilant. In addition, the vaporizers 514 and 524 may be connected to the chambers 511 and 521 to supply air and a sterilant.

In addition, the vaporizers 514 and 524 may be connected to the independent pump module 530 to perform independent pressure control through which pressures of the vaporizers 514 and 524 are controlled, thereby controlling pressures of the impermeable wrappers 512 and 522.

According to an embodiment, the independent pump module 530 may be connected to the chambers 511 and 521, the wrappers 512 and 522, or the vaporizers 514 and 524 to inject air or exhaust air. Through this, each of the chambers 511 and 521, the wrappers 512 and 522, and the vaporizers 514 and 524 may be independently pressure controlled.

According to another preferred embodiment, the vaporizers 514 and 524 supply air to the wrappers 512 and 522 through vaporization to increase internal heating efficiency.

According to another preferred embodiment, the vaporizers 514 and 524 include an exhaust port (not shown) for exhausting the sterilant supplied to the chambers 511 and 521 or the impermeable wrapper 512 and 522, and the exhaust port is connected to a plasma source or a catalyst.

According to an embodiment, the independent pump module 530 also includes an inlet port, and the inlet port is connected to the same or separate plasma source or catalyst.

According to an embodiment, the first chamber module 510 and the second chamber module 520 may include a plurality of valves (not shown). This valve opens and closes when exhausting the wrappers 512 and 522 and the chambers 511 and 521, through which a sterilant is injected and exhausted, and the impermeable wrappers 512 and 522 and the chambers 511 and 521 may be vented in a standby state.

According to another embodiment, the second chamber module 520 may be configured to be connected to a second independent pump module (not shown) connected to a third chamber module (not shown).

In this case, the second chamber module 520 may be exhausted by one or both of the independent pump module 530 and the second independent pump module.

According to an embodiment, the second chamber module 520, as a sterilization process is performed in the first chamber module 510 and the third chamber module (not shown), may select any one of the independent pump module 530 and the second independent pump module considering information on which the independent pump module 530 and the second independent pump module operate, or exhaust both the independent pump module 530 and the second independent pump module.

According to an embodiment, the second chamber module 520 may select one of the independent pump module 530 and the second independent pump module, which is not exhausted, to be connected and exhausted.

Figure 6:
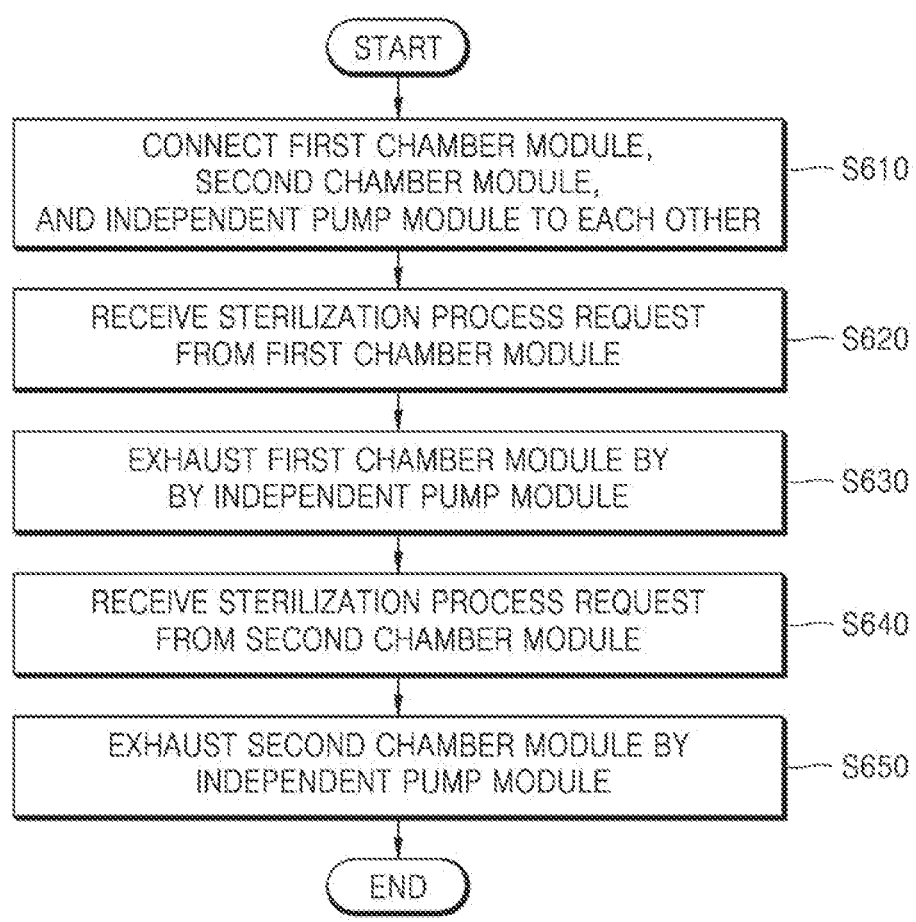
FIG. 6 is a flowchart illustrating an exemplary set of operations by which the sterilization system of FIG. 5 may perform a sterilization operation.

FIG. 6 is a flowchart illustrating an exemplary set of operations by which the sterilization system of FIG. 5 may perform a sterilization operation.

Referring to FIG. 6, the sterilization method according to an embodiment includes operation S610 of connecting a first chamber module, a second chamber module, and an independent pump module, operation S620 of receiving a sterilization process request from the first chamber module, operation S630 of exhausting the first chamber module by the independent pump module, operation S640 of receiving a sterilization process request from the second chamber module, and operation S650 of exhausting the second chamber module by the independent pump module.

According to an embodiment, operation S610 includes connecting and fixing an upper surface or a side surface of the first chamber module and a lower surface or a side surface of the second chamber module by a combining structure, or connecting and fixing an upper surface or a side surface of the first chamber module and a lower surface or a side surface of the second chamber module by a combining structure.

According to an embodiment, the independent pump module receives power by connecting the first chamber module to a power supply line, and is connected to the first chamber module and the second chamber module through a diverging tube.

According to an embodiment, operation S650 further includes obtaining information related to the request for a sterilization process of the second chamber module, and defining an operation schedule for injecting or exhausting air from the first chamber module and/or the second chamber module by closing or opening a diverging point of a tube.

According to another embodiment, operation S630 further includes exhausting a chamber of the first chamber module, extracting and vaporizing a sterilant and injecting the sterilant into the chamber of the first chamber module, exhausting the sterilant from the chamber of the first chamber module, and venting the chamber of the first chamber module.

Figure 7:
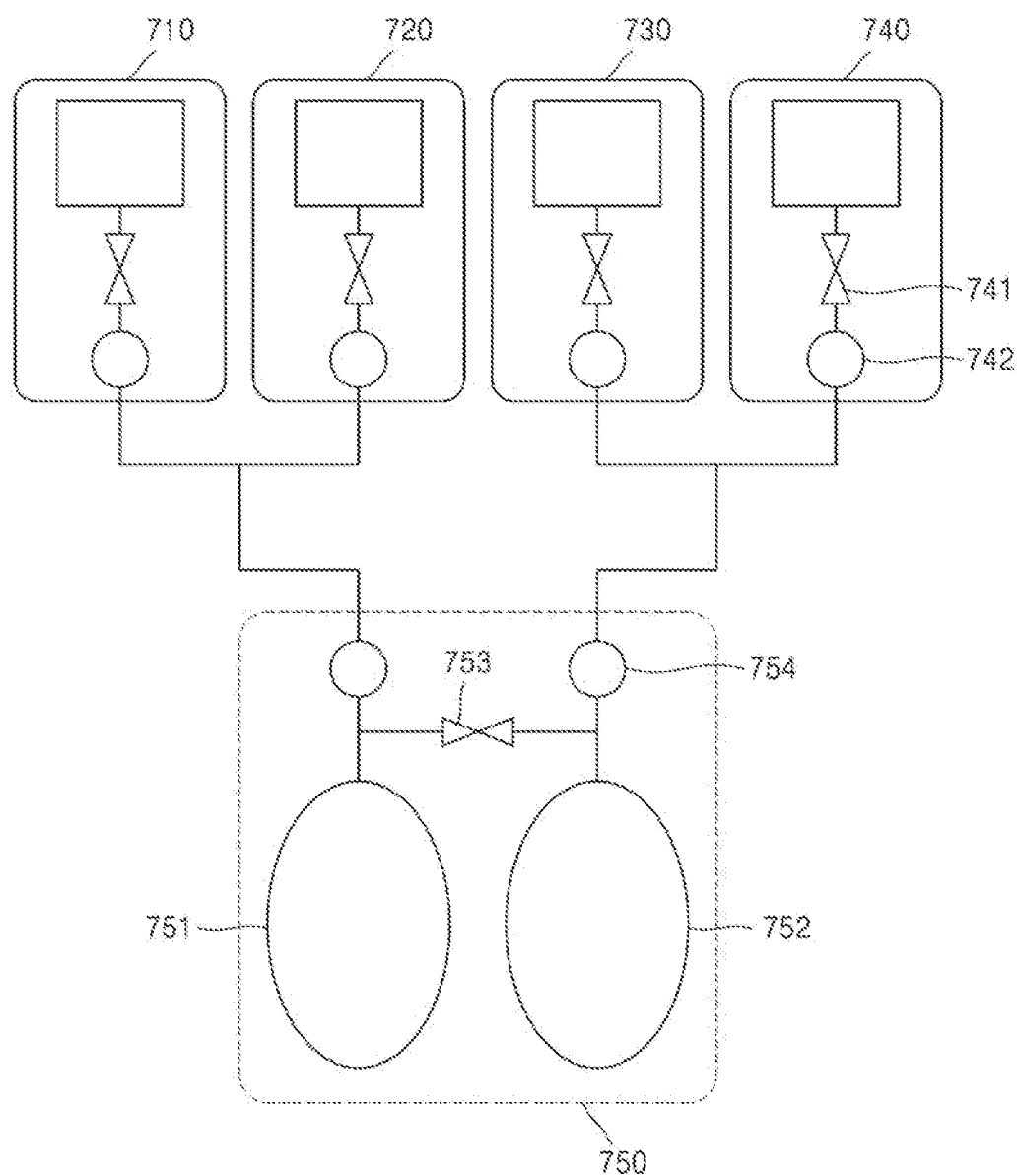
FIG. 7 is a schematic view of a sterilization system, as another example according to the present disclosure.

FIG. 7 is a schematic view of a sterilization system, as another example according to the present disclosure. Referring to FIG. 7, the sterilization system is configured such that four chamber modules 710, 720, 730, and 740 are connected to an independent pump module 750 including two pumps 751 and 752.

According to an embodiment, each of the chamber modules 710, 720, 730, and 740 may include a backflow prevention module 741 such as a check valve in an exhaust line connected to the independent pump module 750 to perform exhaust.

Such a backflow prevention module may also be provided in a tube to which each of the pumps 751 and 752 of the independent pump module 750 is connected.

In addition, each of the chamber modules 710, 720, 730, and 740 may include a plasma source 742 in the exhaust line connected to the independent pump module 750 to perform exhaust.

According to an embodiment, the independent pump module 750 may include a plasma source 754 in an inlet line connected to each of the chamber modules 710, 720, 730, and 740.

According to an embodiment, the independent pump module 750 is connected to the plasma source 754 or a catalyst that neutralizes a sterilant, and the chamber modules 710, 720, 730, and 740 exclude the plasma source 742, and thus a more integrated facility configuration is possible.

According to a preferred embodiment, the first pump 751 of the independent pump module 750 may be connected to the first chamber module 710 and the second chamber module 720, and the second pump 752 may be connected to the third chamber module 730 and the fourth chamber module 740, and exhaust for each connected chamber may be performed through each pump.

According to an embodiment, the first pump 751 and the second pump 752 may be connected to each other by a tube equipped with a backflow prevention module 753 so that exhaust through the first pump 751 may also be performed in the third chamber module 730 or the fourth chamber module 740.

Through this, when only some of the chamber modules 710, 720, 730, and 740 require exhaust, it is possible to control to drive all pumps or only some pumps.

FIG. 8 is a block diagram of a sterilization system 800 according to an embodiment.

FIG. 8, for convenience of explanation, shows a chamber module 810 in which a sterilization process is performed through the sterilization system 800 according to an embodiment, a pump module 820 that exhausts the chamber module 810, and a connector 830 that connects the chamber module 810 to the pump module 820 and through which exhausted air flows.

The sterilization system 800 according to an embodiment may be referred to as a chemical sterilizer, a medical sterilizer, a low-temperature plasma sterilizer, or the like.

Referring to FIG. 8, the sterilization system 800 may include the chamber module 810 equipped with a chamber 811 in which an object to be sterilized is received and a sterilant is supplied to sterilize the object, the pump module 820 equipped with a pump 821 exhausting the air inside the chamber 810, and the connector 830 that connects the chamber module 810 to the pump module 820 and through which internal air flows.

According to an embodiment, in the sterilization system 800, the chamber module 810 and the pump module 820 may be independently apart from each other and may be arranged in an exterior form.

According to an embodiment, in the sterilization system 800, the arrangement of the chamber module 810 and the pump module 820 may be independently changed depending on the shape and adjustment of the connector 830.

According to an embodiment, the chamber module 810 may include the chamber 811 in which a target object is stored, and a path 812 through which the connector 830 connected from the outside of the chamber module 810 leads into the inside of the chamber module 810 and is connected to the chamber 811.

The chamber 811 may include a space capable of being sealed in which a target object is stored.

The path 812 may be a path through which internal air of the chamber 811 flows through the connector 830 when the internal air of the chamber 811 is exhausted by connecting the chamber 811 to the connector 830.

According to an embodiment, the pump module 820 may include the pump 821 for inhaling, and a path 822 through which the connector 830 connected from the outside of the pump module 820 leads into the pump module 820 and is connected to the pump 821.

The pump 821 is connected to the path 822 to suck air in a desired place, and may be a vacuum pump according to an embodiment.

The path 822 may be a path that connects the pump 821 to the connector 830 so that air flowing in the connector 830 may be moved to the pump 821 by the operation of the pump 821.

Air in the present specification does not mean only the atmosphere, but may mean a gas in a specific space that may have a different composition ratio from the atmosphere. In addition, the air in the present specification may include a material in a liquid state or a material in a solid state that may be circulated with gas. For example, the air inside a chamber in the present specification may include not only a gas in the chamber, but also a sterilant or contaminants attached to a target object.

According to an embodiment, the connector 830 may be a path through which the internal air of the chamber module 810 inhaled by the pump module 820 flows by connecting the chamber module 810 to the pump module 820.

Figure 9B:
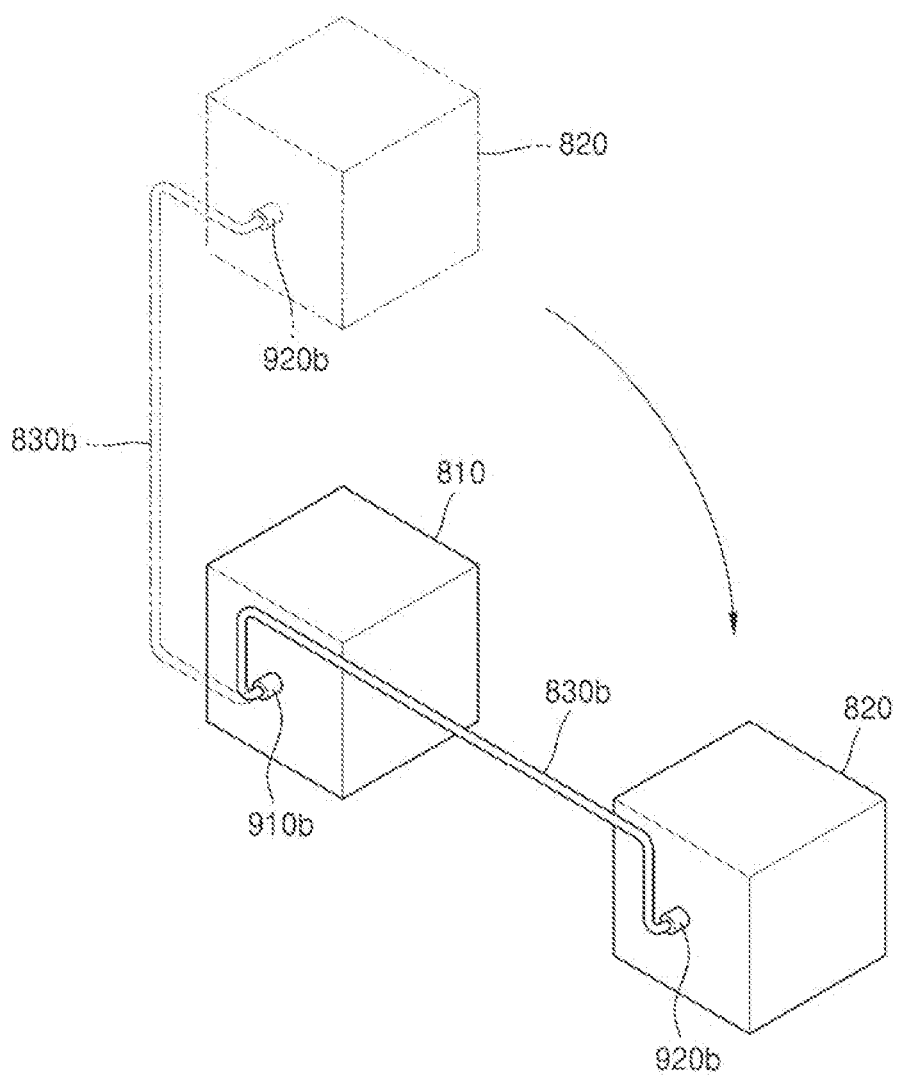
Figure 9C:
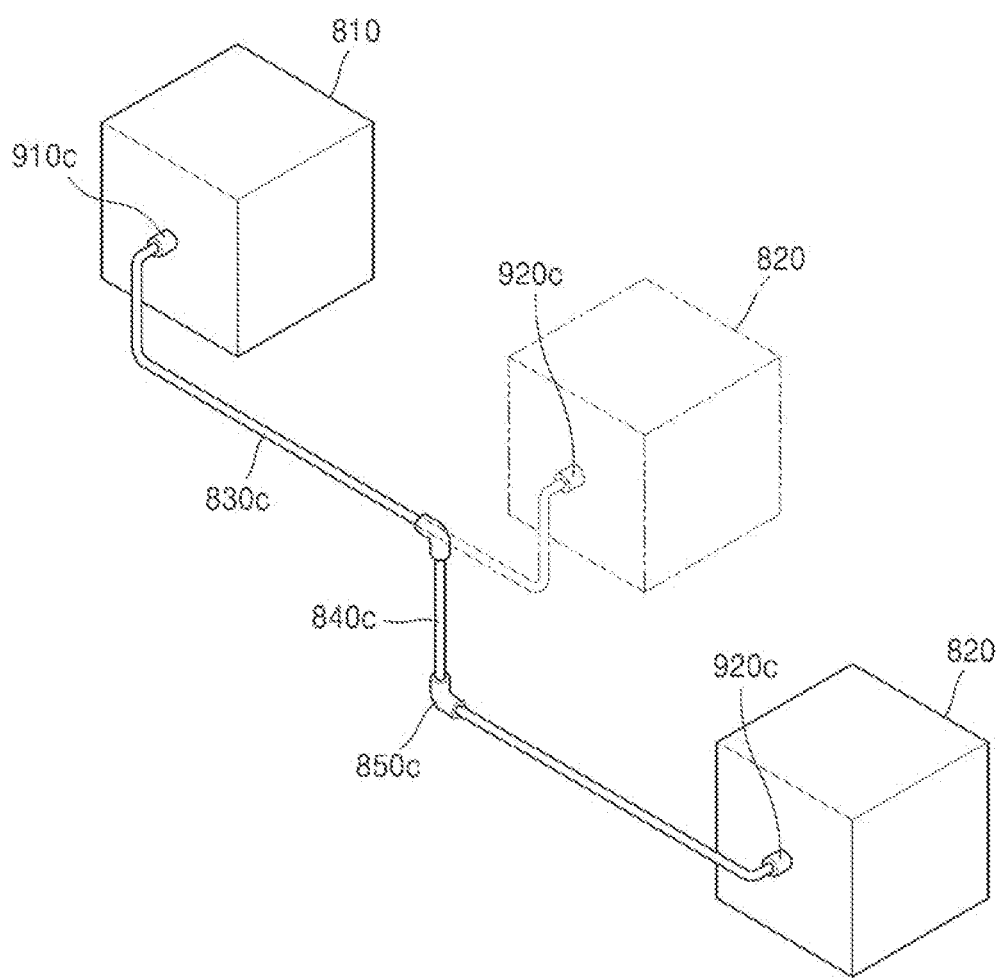

FIGS. 9A to 9C are views for explaining a change in an arrangement between a chamber and a pump in a sterilization system according to an embodiment.

Referring to FIG. 9A, a connector 830a connects the chamber module 810 to the pump module 820, and may have a hollow tube shape inside.

According to an embodiment, the position of a point 910a where the connector 830a is connected to the chamber module 810 is fixed, but rotation is free. Accordingly, when the chamber module 810 is used as a reference, the arrangement of the pump module 820 and the chamber module 810 may be changed by rotating the connector 830a around the connection point 910a.

According to an embodiment, the location of the point 910a connected to the chamber module 810 may be changed. For example, the point 910a may be provided with a path such that the point 910a may be moved in a vertical direction, left and right directions of the chamber module 810, or in a longitudinal direction of the connector 830a, or may include an elastic material.

In addition, according to an embodiment, because the connector 830a includes a flexible material and may freely change its shape, the position of the pump module 820 may be more variously changed with respect to the chamber module 810.

In addition, according to an embodiment, the connector 830a is elastic or has a structure that extends or contracts in a longitudinal direction, so that the position of the pump module 820 may be more freely changed with respect to the chamber module 810.

According to an embodiment, the connector 830a made of a flexible material may have a support frame 920a made of a hard material.

The support frame 920a has a spring shape and is located inside or outside the connector 830a to prevent damage or shape change of the connector 830a by air flowing inside the connector 830a.

According to an embodiment, in the support frame 920a, a plurality of rings may be located continuously in the length direction of the connecting portion 830a or apart from each other at certain intervals, or bands extending in the longitudinal direction of the connecting portion 830a may be located continuously or apart from each other at certain intervals in a circumferential direction of the connecting portion 830a.

Referring to FIG. 9B, a connector 830b may connect the chamber module 810 to the pump module 820, and may have a hollow tube shape and include a solid material, and the shape may be fixed.

According to an embodiment, the location of a point 910b where the connector 830b is connected to the chamber module 810 and the shape of the connector 830b are fixed, but the connector 830b may be rotated freely. When the chamber module 810 is referenced, the arrangement of the pump module 820 may be changed by rotating the connector 830b around the point 910b to which the pump module 820 is connected.

In addition, according to an embodiment, the connector 830b may change the position of the connection point 910b and extend or contract the connection point 910b in the longitudinal direction, in the same manner as the change in the embodiment of the connection portion 830a.

Referring to FIG. 9C, a connector 830c may connect the chamber module 810 to the pump module 820, may have a hollow tube shape and include a solid material, and the shape may change.

According to an embodiment, the shape of the connector 830c may be determined when the sterilization system 800 is arranged. For example, the connector 830c includes a hard material and has a hollow tube shape, and may be connected to a long tube 840c and a binder 850c that is bonded to the tube 840c to rotate the tube in a direction at a certain angle. At this time, the shape may be determined while connecting tubes 840c of various lengths with the binder 850c rotating the direction at various angles. According to an embodiment, the number and connection structure of connectors, tubes, and binders may be variously modified.

Through this, the connector 830c may enable various arrangements between the chamber module 810 and the pump module 820.

According to an embodiment, the connector 830c may rotate after the shape is fixed by a combination of the tube 840c and the binder 850c. At this time, a connection point 910c may be changed in position, and may be extended or shortened in a longitudinal direction.

According to an embodiment, the connector 830 may be formed of a combination of a connector made of a flexible material and a connector made of a hard material.

According to an embodiment, the connector 830 may include a hard material inside a path through which internal air flows.

According to an embodiment, the hard material included in the inside of the path through which internal air flows may have chemical resistance.

According to an embodiment, the connector 830 may include a hard material or a material having chemical resistance inside the path through which the internal air flows, to prevent damage or deformation by a material contained in the internal air circulating inside the path (e.g., a residual sterilant, etc.).

Through this, even if sterilization is repeatedly used, there is no damage or deformation in the connector 830, and repeat reliability may be secured.

According to an embodiment, the connector 830 may include a hard material inside the path through which internal air flows.

Through this, the connector 830 may prevent damage or defects due to an external physical impact.

For example, when a path is damaged or deformed, the pumping speed is lowered, resulting in a problem of lowering the sterilization reliability. Accordingly, the connector 830 may solve the problem of lowering the sterilization reliability by including a hard material or a material having chemical resistance inside or outside the path through which the internal air flows.

According to an embodiment, a length of the connector 830 may be within 1.5 m. When the length of the connector 830 is increased, pumping by the pump module 820 cannot be effectively transmitted to the chamber module 810, and thus, the length of the connector 830 cannot exceed a maximum of 1.5 m in order to meet the effective pumping speed required in a sterilization process. However, a maximum length of the connector 830 may vary depending on the pumping speed, the volume of a chamber, and the volume of an effective object to be sterilized.

According to an embodiment, the connector 830 may be a tube cable through which air flows.

According to an embodiment, the sterilization system 800 may further include a controller (not shown) to derive information related to a length of the connection unit 830 using a user input or a value measured through a pumping operation (e.g., a pumping time to reach a specific pressure level, a pressure value measured inside the chamber 811, the pump 821, or the connector 830, etc.), and may control at least one of a pumping speed, a pumping time, and a pumping intensity to be operated during a sterilization process, a driving time for each operation of the sterilization process, and a waiting time for each operation of the sterilization process using information related to the length.

According to an embodiment, the connector 830 includes a backflow prevention module, and prevents air flowing from the chamber module 810 to the pump module 820 from flowing back to the chamber module 810 from the pump module 820.

According to an embodiment, a controller (not shown) controls an operation of the pump 821 by using information related to the length of the connection unit 830.

According to an embodiment, the controller (not shown) controls the operation intensity or operation time of the pump.

According to an embodiment, the controller (not shown) performs a test run mode in which the pump module 820 is operated at a preset reference value with respect to the operation intensity or operation time.

According to an embodiment, the controller (not shown) may determine suitability of the arrangement of the pump module 820 according to the connection unit 830 through the test run mode.

According to an embodiment, in determining the suitability, the controller (not shown) may determine whether the operation of the pump module 820 is sufficient to exhaust the air inside the chamber module 810 through the amount of exhaust or the exhaust time.

According to an embodiment, the controller (not shown) may determine the operation intensity or operation time of the pump module 820 in an operation mode excluding the test run mode, based on the amount of exhaust or the exhaust time measured through the test run mode.

Figure 10:
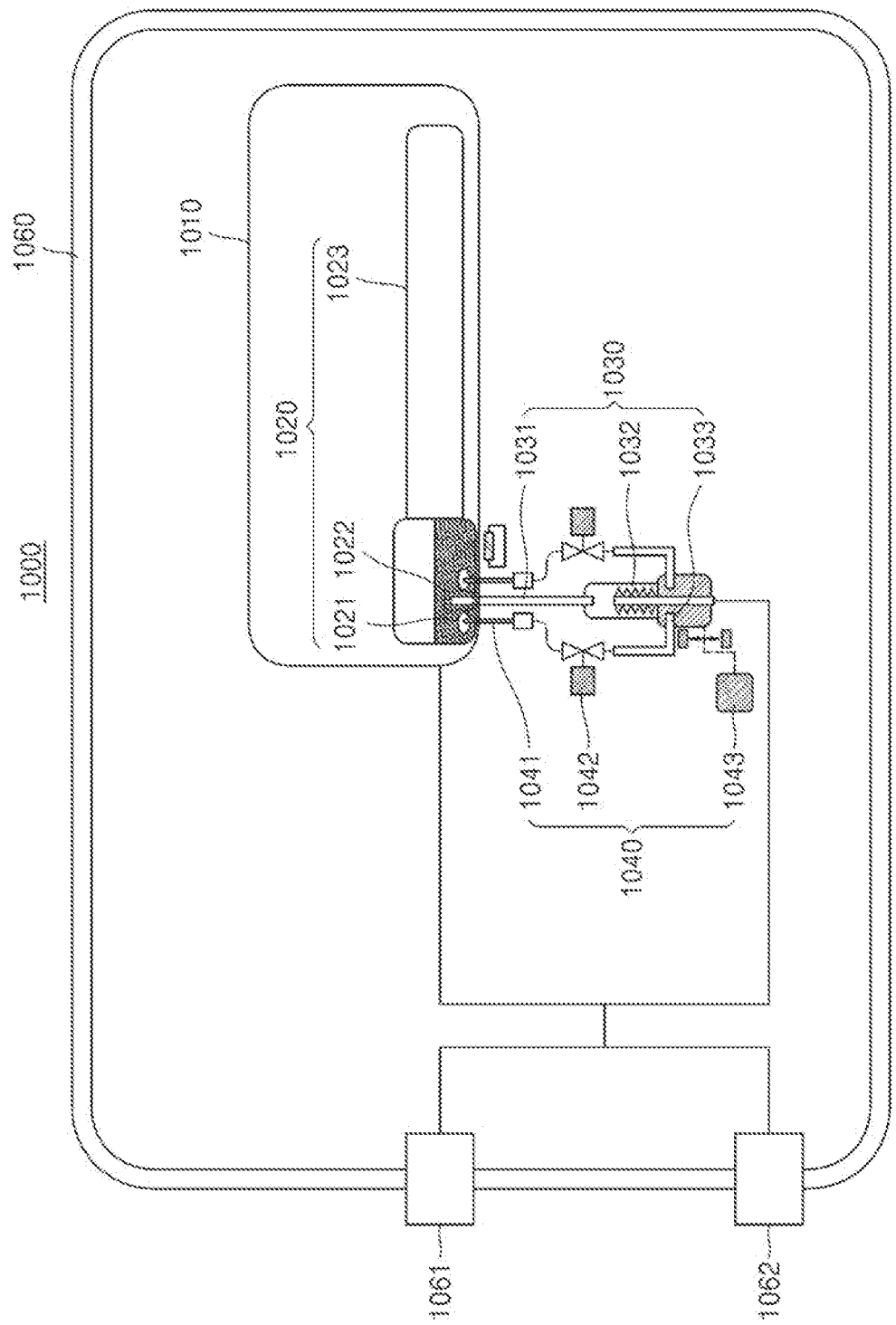
FIG. 10 is a block diagram of a chamber module according to an embodiment.
Figure 11:
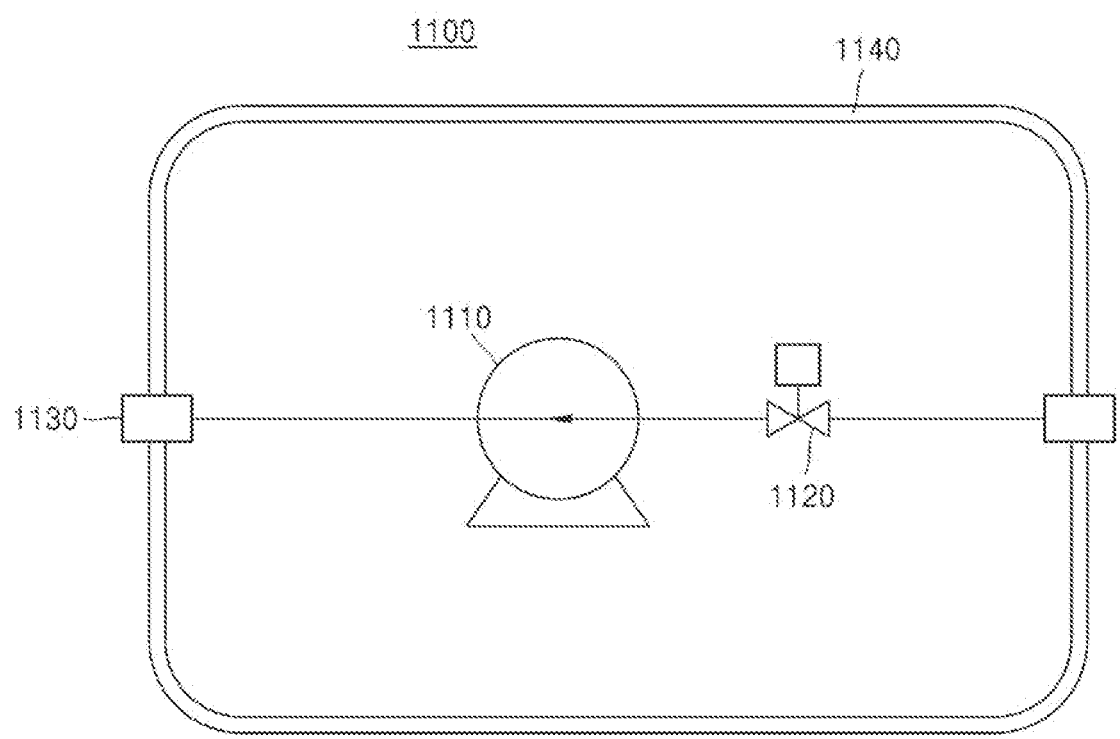
FIG. 11 is a block diagram of a pump module according to an embodiment.

FIG. 10 is a block diagram of a chamber module according to an embodiment, and FIG. 11 is a block diagram of a pump module according to an embodiment.

Referring to FIGS. 10 and 11, a chamber module 1000 includes a chamber 1010, a cartridge 1020, a sterilant provider 1030, a sterilant extractor 1040, a connection pipe 1050, and a chamber housing 1060.

According to an embodiment, the chamber module 1000 may be selectively operated in a chamber mode in which sterilization is performed by receiving an object to be sterilized (target object) in the chamber 1010 and a pouch mode in which sterilization is performed by receiving a target object in a wrapper 1023 of the cartridge 1020.

According to an embodiment, the chamber 1010 may be a structure for receiving an object to be sterilized (target object) inside, or for supporting or receiving the cartridge 1020. According to an embodiment, the chamber 1010 may be sealed such that the inside thereof can be depressurized.

The cartridge 1020 may include a sterilant container 1021, an injector 1022, and a wrapper 1023.

According to an embodiment, the cartridge 1020 may be fixed to the chamber 1010.

According to an embodiment, the sterilant container 1021 has a certain internal space to store a sterilization agent used for sterilization, and stores a sterilant such as hydrogen peroxide therein. The sterilant container 1021 may be sealed with a sealing material such that the stored sterilant does not leak. At this time, the sealing material may have elasticity so that a path (e.g., a hole created by a pointed object such as a needle penetrating through it) through which the sterilant is distributed may be closed again on an outer surface of the sterilant container 1021 for extraction of the sterilant.

According to an embodiment, the sealing material may be made of elastic silicone, rubber, synthetic resin, etc., and may be formed of a material that can be penetrated by sharp objects without chemical reaction with a sterilant.

In addition, as another embodiment, the sterilant container 1021 may further include a film between a sealing material and a sterilant storage space to prevent leakage of a sterilant. According to an embodiment, the film may include a material that does not undergo a chemical reaction with a sterilant and may be penetrated by a pointed object.

The injector 1022 is used to supply a sterilant to the chamber 1010 or the wrapper 1023 through the cartridge 1020 or to depressurize the interior of the wrapper 1023. To achieve this function, the injector 1022 includes a path connected to the chamber 1010 or the wrapper 1023.

The injector 1022 may be penetrated by a pointed object such as a needle, and may include a sealing material having elasticity such that a through-penetrating portion is closed again after the sterilant is supplied or exhaust for decompression is performed and the wrapper 1023 returns to a sealed state.

The wrapper 1023 is combined to be sealed to the body of the cartridge 1020 and a target object is stored therein. However, the chamber module 1000 operated only in the chamber mode described above may be configured without the wrapper 1023.

According to an embodiment, the wrapper 1023 has an open side for storage before a target object is received, but after the target object is received, the open side is sealed and adhered. For example, the wrapper 1023 may have an open side sealed by a thermocompression method.

According to an embodiment, the cartridge 1020 may further include a tag (not shown). The tag refers to a mark such as a barcode or a QR code that may check information about the cartridge 1020, and may be formed on one side of the cartridge 1020 so that the sterilization system may check it.

The sterilant provider 1030 may include a pipe 1033 receiving a sterilant extracted from the sterilant extractor 1040, a vaporizer 1032 heating and vaporizing the sterilant received through the pipe 1033, and a needle 1031 penetrating a sealing material sealing the injector 1022.

The sterilant extractor 1040 may include a needle 1041 penetrating the sealing material sealing the sterilant container 1021, a first valve 1042 controlling a sterilant flow, and a driver 1043 moving the needle 1041 in a vertical direction.

The chamber housing 1060 is a case of a chamber module. The chamber housing 1060 protects internal parts constituting the chamber module from external shocks. The chamber housing 1060 is a space that is separated from the outside to prevent a sterilization process from being affected by the external environment. In particular, the chamber housing 1060 may separate the chamber module 1000 from a pump module 1100 into an independent and individual device, and may be independently arranged to be less affected by the pump module 1100.

According to an embodiment, the chamber housing 1060 further includes a combiner 1061 to which a connector for connecting the chamber module 1000 to the pump module 1100 is combined.

According to an embodiment, the combiner 1061 may be configured to have a fixed position and move in a vertical direction, a left-right direction, or a depth direction.

The pump module 1100 may include a pump 1110, a second valve 1120 controlling a gas flow, a filter 1130, and a pump housing 1140.

The filter 1130 is connected to the pump 1110 or is installed at a portion through which external and internal air of the pump housing 1140 flows, and when a gas exhausted from the chamber module 1000 is discharged to the outside by driving the pump 1110, filters harmful components included in the gas. According to an embodiment, the filter 1130 may be a deodorant filter or an ozone (03) filter for purifying a sterilant component included in the gas or contaminants separated from a target object.

The pump housing 1140 is a case of a pump module. The pump housing 1140 protects internal parts constituting the pump module from external shocks, and is a space separated from the outside at a certain interval.

According to an embodiment, the pump housing 1140 further includes a fan for discharging the air inside the pump module 1100 to the outside. According to an embodiment, the pump module 1100 may include the filter 1130 in a path through which internal air is discharged to the outside.

Figure 12:
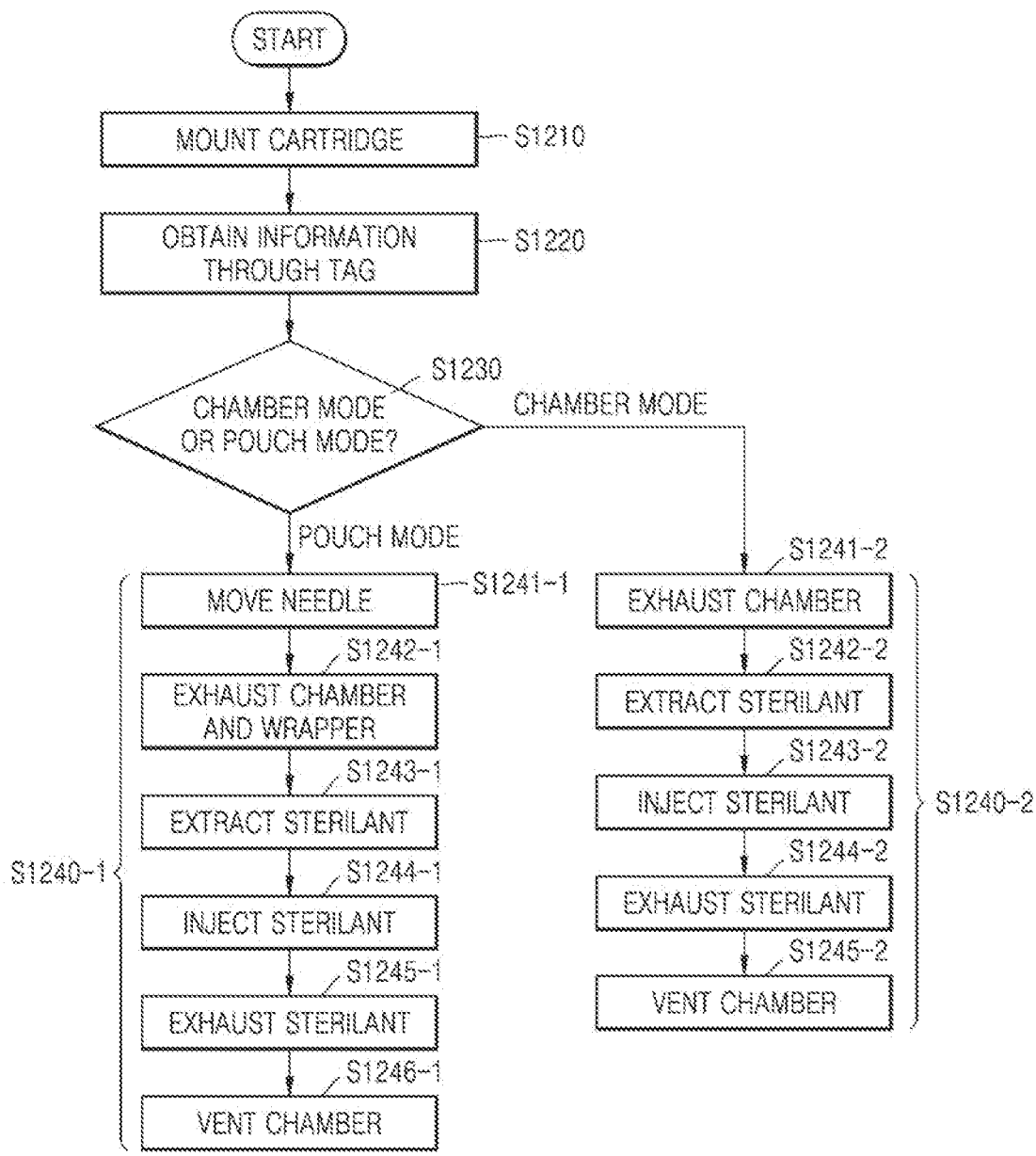
FIG. 12 is a flowchart showing a sterilization method according to an embodiment.

FIG. 12 is a flowchart showing a sterilization method according to an embodiment.

Referring to FIG. 12, a sterilization method according to an embodiment includes operation S1210 of mounting the cartridge 1020 to the chamber module 1000 of a sterilization system, operation S1220 of obtaining information through a tag (not shown) displayed on the cartridge 1020, operation S1230 of selecting whether a chamber mode or a pouch mode, operation S1240-1 of performing sterilization in the pouch mode, and operation S1240-2 of performing sterilization in the chamber mode.

In operation S1210, the cartridge 1020 is mounted on the chamber module 1000 of the sterilization system. According to an embodiment, the wrapper 1023 of the cartridge 1020 or the chamber 1010 of the chamber module 1000 stores an object to be sterilized (target object).

According to an embodiment, in operation S1210, the sterilization system receives information about whether the target object is stored in the wrapper 1023 of the cartridge 1020 or the chamber 1010 of the chamber module 1000.

In operation S1220, the sterilization system may determine whether the cartridge 1020 is genuine or reused by using the information obtained through the tag (not shown). According to an embodiment, in operation S1220, the sterilization system uses the information obtained through the tag (not shown) to provide information about whether the target object is stored in the wrapper 1023 of the cartridge 1020 or the chamber 1010 of the chamber module 1000.

In operation S1230, the sterilization system selects whether a sterilization operation is in the chamber mode or the pouch mode by using at least one of a user input, information obtained from the cartridge, information about whether the target object is stored in the chamber or the wrapper, or information about whether the wrapper is attached to the cartridge. According to an embodiment, the sterilization system selects whether the sterilization operation is in the chamber mode or the pouch mode by using information about whether the target object is stored in the wrapper 1023 of the cartridge 1020 or the chamber 1010 of the chamber module 1000, the information being extracted in operation S1220.

In the chamber mode, the chamber 1010 is used as a space where a sterilization process in which a sterilant is injected is performed, and in the pouch mode, the wrapper 1023 is used as a space where a sterilization process in which a sterilant is injected is performed.

The sterilization system performs operation S1240-1 of performing sterilization in the pouch mode when the pouch mode is selected in operation S1230, and operation S1240-2 of performing sterilization in the chamber mode when the chamber mode is selected in operation S1230.

Operation S1240-1 of performing sterilization in the pouch mode includes operation S1241-1 of moving a needle, operation S1242-1 of exhausting the chamber and the wrapper, operation S1243-1 of extracting a sterilant, operation S1244-1 of injecting the sterilant into the wrapper, operation S1245-1 of exhausting the sterilant from the wrapper, and operation S1246-1 of venting the chamber and the wrapper.

In operation S1241-1, the driver 1043 of the sterilization system moves the needle 1041 of the sterilant extractor 1040 and the needle 1031 of the sterilant provider 1030 in a direction of the cartridge 1020 to penetrate a sealing material of the sterilant container 1021 and a sealing material of the injector 1022. According to an embodiment, the driver 1043 may be configured to independently and individually move the needle 1041 of the sterilant extractor 1040 and the needle 1031 of the sterilant provider 1030.

According to an embodiment, before performing operation S1241-1, the sterilization system may secure airtightness of the chamber 1010 by exhausting the air inside the chamber 1010 as in operation S1241-2. For example, the chamber 1010 may include a chamber door (not shown), open the chamber door to receive the target object, and close the chamber door to seal the chamber door. At this time, in the sterilization system, when the chamber door containing the target object is closed, the air inside the chamber 1010 is exhausted to make the chamber door more tightly contacted, thereby securing the closure.

The sterilization system exhausts the gas inside the wrapper 1023 through an inner tube of the needle 1031 of the sterilant provider 1030 or a path of the injector 1022 according to operations (the first valve 1042 is closed and the second valve 1120 is open) of the pump 1110, the first valve 1042 of the sterilant extractor 1040, and the second valve 1120 of the pump module 1100 after connecting the sterilant provider 1030 to the pump 1110 to reduce pressure. According to an embodiment, in operation S1242-1, the sterilization system may further exhaust air inside the chamber 1010 by connecting the chamber 1010 to the pump 1110. According to an embodiment, the sterilization system may simultaneously exhaust air from the wrapper 1023 and the chamber 1010.

In operation S1243-1, the sterilization system, after connecting the sterilant extractor 1040 to the pump 1110, extracts a sterilant stored in the sterilant container 1021 by using a pressure difference through an inner tube of the needle 1041 of the sterilant extractor 1040 according to operations (the first valve 1042 is open and the second valve 1120 is closed) of the pump 1110, the first valve 1042 of the sterilant extractor 1040, and the second valve 1120 of the pump module 1100 after connecting the sterilant provider 1030 to the pump 1110.

In operation S1244-1, the sterilization system transfers the extracted sterilant to the vaporizer 1032 through the needle 1031 of the sterilant provider 1030 by using a pressure difference or gravity, and injects the sterilant vaporized in the vaporizer 1032 into the wrapper 1023 through the inner tube of the needle 1031 of the sterilant provider 1030 or the path of the injector 1022 of the cartridge 1020 by using a pressure difference. Through this, the sterilization system sterilizes the target object by spreading and moving the vaporized sterilant into the wrapper 1023.

According to an embodiment, in operation S1242-1, a connection pipe of the sterilization system connects a gas exhausted by the connected pump module 1100 to the chamber 1010 and depressurizes the chamber 1010 to inflate the wrapper 1023, so that a sterilant may be more easily injected or diffused. In operation S1244-1, in the sterilization system, when a path through which the sterilant is distributed through the inner tube of the needle 1031 of the sterilant provider 1030 or the path of the injector 1022 of the cartridge 1020 is formed, internal pressure of the wrapper 1023 is greater than internal pressure of the chamber 1010, the wrapper 1023 expands to secure a certain volume, and the sterilant spreads into the wrapper 1023 by this pressure difference.

In operation S1245-1, the sterilization system exhausts the gas and sterilant inside the wrapper 1023 through the inner tube of the needle 1031 of the sterilant provider 1030 or the path of the injector 1022 according to operations (the first valve 1042 is closed and the second valve 1120 is open) of the pump 1110, the first valve 1042 of the sterilant extractor 1040, and the second valve 1120 of the pump module 1100. According to an embodiment, the pump module 1100 places the filter 1130 in a path through which the exhausted gas and sterilant are discharged to the pump module to purify and discharge the exhausted gas and sterilant. According to an embodiment, the chamber module 1000 may decompose the sterilant by placing a plasma processing unit (not shown) in an exhaust path.

In operation S1246-1, the sterilization system vents the chamber 1010 and vents the wrapper 1023 using the needles 1031 and 1041. According to an embodiment, a filter (not shown) may be provided in a path through which external air for venting the chamber 1010 and the wrapper 1023 is introduced.

According to an embodiment, in operation S1246-1, the sterilization system vents the chamber 1010 and does not vent the wrapper 1023, so that the wrapper 1023 may be assured of sterility.

According to an embodiment, the sterility assurance may be vacuum sealing.

According to an embodiment, in operation S1246-1 step, the sterilization system may return the needles 1031 and 1041 to their original positions.

Operation S1240-2 of performing sterilization in the chamber mode includes operation S1241-2 of exhausting the air inside the chamber 1010, operation S1242-2 of extracting a sterilant, operation S1243-2 of injecting the sterilant into a chamber, operation S1244-2 of exhausting the sterilant from the chamber, and operation S1245-2 of venting the chamber.

In operation S1241-2, the sterilization system connects the chamber 1010 to the pump 1110 and exhausts the air inside the chamber 1010 by driving the pump 1110 to lower internal pressure of the chamber 1010.

In operation S1242-2, the sterilization system, after connecting the sterilant extractor 1040 to the pump 1110, extracts the sterilant stored in the sterilant container 1021 by using a pressure difference through the inner tube of the needle 1041 of the sterilant extractor 1040 according to operations (the first valve 1042 is open and the second valve 1120 is closed) of the pump 1110, the first valve 1042 of the sterilant extractor 1040, and the second valve 1120 of the pump module 1100 after connecting the sterilant provider 1030 to the pump 1110.

According to an embodiment, the sterilization system may define operations S1243-1 and S1242-2 as the same operation.

In operation S1243-2, the sterilization system transfers the extracted sterilant to the vaporizer 1032 through the needle 1031 of the sterilant provider 1030 by using a pressure difference or gravity, and injects the sterilant vaporized in the vaporizer 1032 into the chamber 1010 through the inner tube of the needle 1031 of the sterilant provider 1030 or the path of the injector 1022 of the cartridge 1020 by using a pressure difference. Through this, the sterilization system diffuses and moves the vaporized sterilant into the chamber 1010 to sterilize a target object stored in the chamber 1010. At this time, by operation S1241-2, as the sterilant is introduced into the chamber 1010 in a state where internal pressure is low, the sterilant may spread better.

According to an embodiment, the sterilization system may define operations S1244-1 and S1243-2 as the same operation.

In operation S1244-2, the sterilization system exhausts the gas and sterilant inside the wrapper 1010 through the inner tube of the needle 1031 of the sterilant provider 1030 or the path of the injector 1022 according to operations (the first valve 1042 is closed and the second valve 1120 is open) of the pump 1110, the first valve 1042 of the sterilant extractor 1040, and the second valve 1120 of the pump module 1100.

In operation S1245-2, the sterilization system vents the chamber 1010.

According to an embodiment, in operation S1245-2, the sterilization system may return the needle 1041 of the sterilant extractor 1040 or the needle 1031 of the sterilant provider 1030 to the original position.

Figure 13:
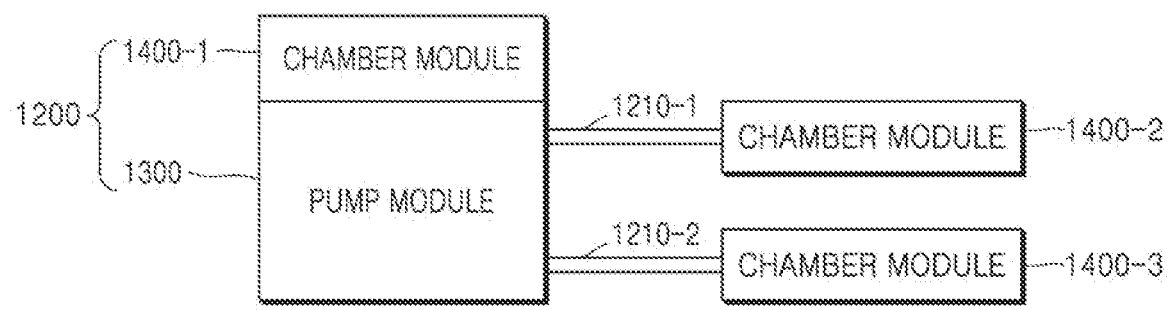
FIG. 13 is a view showing a connection state between a sterilization device and an additional chamber module according to another embodiment.

FIG. 13 is a view showing a connection state between a sterilization device and an additional chamber module according to another embodiment.

Referring to FIG. 13, a sterilization device 1200 according to another embodiment includes a pump module 1300 and a basic chamber module 1400-1, and additional chamber modules 1400-2 and 1400-3 may be selectively connected to the pump module 1300.

The sterilization device 1200 and the additional chamber modules 1400-2 and 1400-3 may be connected to each other to form a single sterilization system.

The pump module 1300 and the additional chamber modules 1400-2 and 1400-3 may be divided into mutually independent modules based on outer housings of the pump module 1300 and the additional chamber modules 1400-2 and 1400-3.

The additional chamber modules 1400-2 and 1400-3 may be configured to be independent from the sterilization device 1200 and may be connected to the pump module 1300 through outer tubes 1210-1 and 1210-2.

Although FIG. 13 illustrates a case in which two additional chamber modules 1400-2 and 1400-3 are connected to the pump module 1300, the number of additional chamber modules 1400-2 and 1400-3 that may be connected to the pump module 1300 may be at least one or more.

According to an embodiment, each of the basic chamber module 1401-1 and the additional chamber modules 1400-2 and 1400-3 may include a chamber (not shown) for receiving a target object, and a vaporizer (not shown) connected to the chamber to supply a vaporized sterilant.

Figure 14:
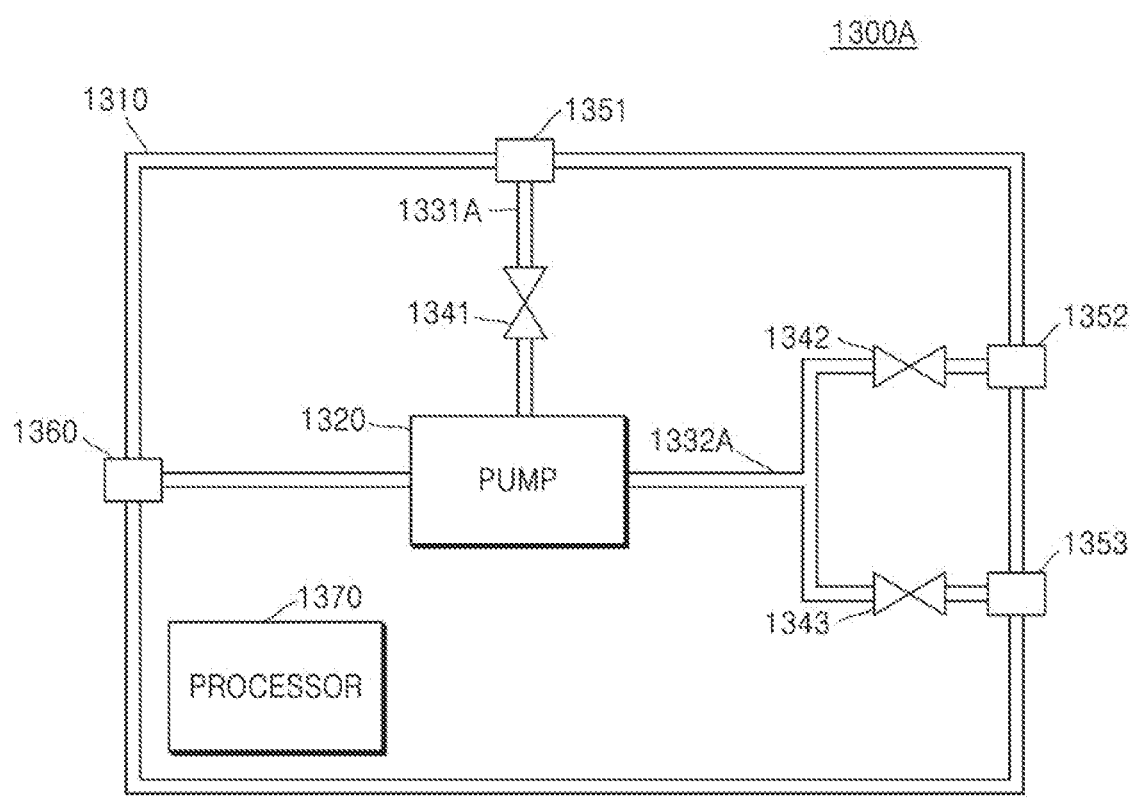
FIG. 14 is a block diagram according to an embodiment of a pump module shown in FIG. 13.

FIG. 14 is a block diagram according to an embodiment of the pump module shown in FIG. 13.

Referring to FIGS. 13 and 14, a pump module 1300A may include a housing 1310, a pump 1320, a plurality of inner tubes 1331A and 1332A, a plurality of valves 1341 to 1343, a first combiner 1351, a plurality of second combiners 1352 and 1353, a filter 1360, and a processor 1315.

The housing 1310 is configured to surround each component (e.g., 1320 to 1370) of the pump module 1300A, may and protect each component (e.g., 1320 to 1370) of the pump module 1300A from external impact.

The pump 1320 is built in the pump module 1300A and intakes internal air from the basic chamber module 1400-1 and one or more additional chamber modules 1400-2 and 1400-3 connected to the pump module 1300A, and may exhaust the internal air to the filter 1360.

According to an embodiment, the pump 1320 may be implemented as a vacuum pump.

The first inner tube 1331A may connect the pump 1320 to the first combiner 1351 to allow internal air to flow.

The first valve 1341 may be arranged in the first inner tube 1331A, and a flow of internal air flowing to the first inner tube 1331A may be controlled by the first valve 1341.

The first combiner 1351 may connect the basic chamber module 1400-1 to the pump module 1300A.

According to an embodiment, the first combiner 1351 may include a structure for physically combining and fixing the basic chamber module 1401-1 and the pump module 1300A.

According to an embodiment, the first combiner 1351 may include a path structure therein so that internal air may be circulated between the basic chamber module 1401-1 and the pump module 1300A through a sealed path.

According to an embodiment, the first combiner 1351 may be connected to a chamber (not shown) through a tube inside the basic chamber module 1401-1.

The second inner tube 1332A may be connected between the pump 1320 and the second combiner 1353 to allow internal air to flow.

According to an embodiment, when at least two additional chamber modules 1400-2 and 1400-3 are connected to the pump module 1300A, the plurality of second combiners 1352 and 1353 may be implemented as shown in FIG. 14. At this time, the second inner tube 1332A diverges to correspond to the number of the plurality of second combiners 1352 and 1353, to connect the pump 1320 to the plurality of second combiners 1352 and 1353, respectively.

The second valves 1342 and 1343 may be arranged in each path diverging from the second inner tube 1332A, and the flow of internal air circulating through the second inner tube 1331A may be controlled by the second valves 1342 and 1343.

The filter 1360 is connected to the pump 1320 or is installed at a portion through which external and internal air of the pump housing 1310 flows, and when a gas exhausted from the chamber modules 1400-1 to 1400-3 is discharged to the outside by driving the pump 1320, filters harmful components included in the gas. For example, the filter 1360 may be a deodorant filter or an $O_3$ filter for purifying a sterilant component included in a gas or contaminants separated from a target object.

The processor 1370 may control a general operation of the pump module 1300A.

According to an embodiment, the processor 1370 may control an open state and a closed state of the plurality of valves 1341 to 1343.

According to an embodiment, when one of the plurality of valves 1341 to 1343 (e.g., 1341) is controlled to be open, the processor 1370 may controls the remaining valves (e.g., 1342 and 1343) to be closed. In this case, the processor 1370 may sequentially open the plurality of valves 1341 to 1343 according to a certain schedule to exhaust the corresponding chamber modules 1401-1 to 1400-3.

According to another embodiment, the processor 1370 may control the first valve 1341 and one of the second valves 1342 and 1343 in an open state, and in this case, any one of the plurality of additional chamber modules 1400-2 and 1400-3 and the basic chamber module 1401-1 may be exhausted together.

According to an embodiment, the processor 1370 may detect the number of one or more additional chamber modules (e.g., 1400-2 and 1400-3) connected to each other through the second combiners 1352 and 1353, and may control at least one of a pumping speed, a pumping intensity, and a pumping time of the pump 1320 depending on the number of detected additional chamber modules (e.g., 1400-2 and 1400-3). For example, as the number of detected additional chamber modules increases, the pumping speed may be increased, the pumping intensity may be increased, or the pumping time may be increased.

According to an embodiment, the pump module 1300A may exhaust internal air from a chamber inside the chamber modules 1400-1 to 1400-3, a pouch arranged to contain an object to be sterilized in the chamber, or a cartridge to which the pouch is combined.

Figure 15:
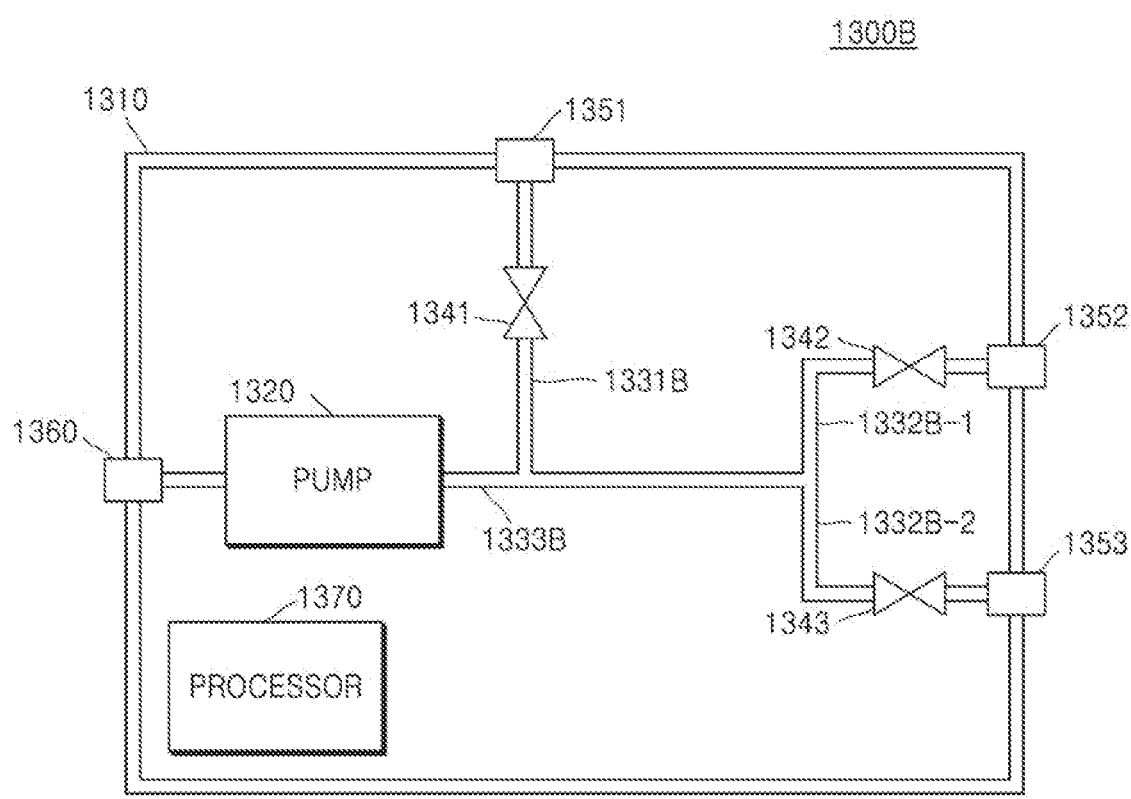
FIG. 15 is a block diagram according to another embodiment of a pump module shown in FIG. 13.

FIG. 15 is a block diagram according to another embodiment of the pump module shown in FIG. 13.

Referring to FIGS. 13 to 15, according to another embodiment of a pump module 1300B, there is a difference in the structure of inner tubes 1331B, 1332B-1, 1332B-2, and 1333B compared to the pump module 1300A of FIG. 14.

The first inner tube 1331B may connect the pump 1320 to the first combiner 1351 to allow internal air to flow.

The second inner tubes 1332B-1 and 1332B-2 may connect the pump 1320 to the second combiners 1352 and 1353 to allow internal air to flow.

The first inner tube 1331B and the second inner tubes 1332B-1 and 1332B-2 may be gathered into one third inner tube 1333B and connected to the pump 1320.

According to an embodiment, the third inner tube 1333B may be additionally provided with a reverse flow prevention module for preventing reverse flow of the internal gas.

Figure 16:
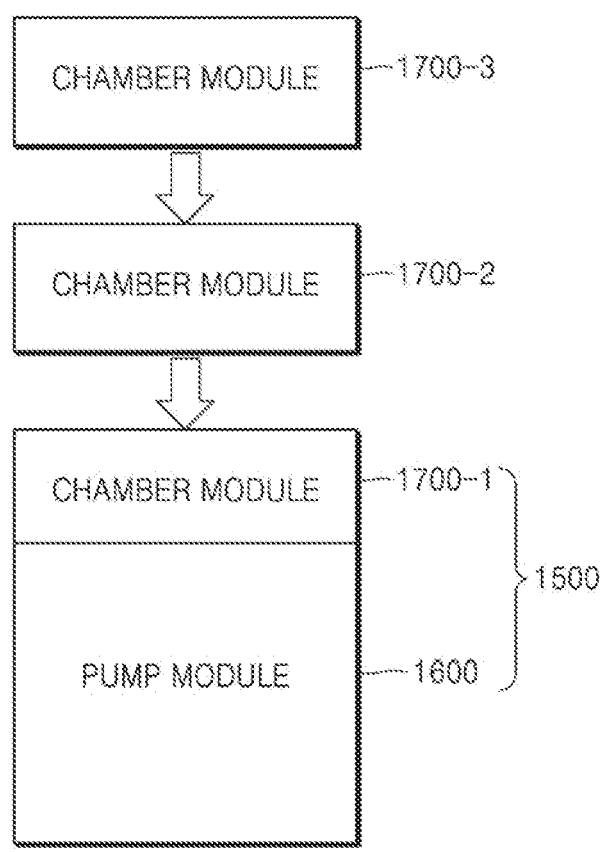
FIG. 16 is a view showing a connection state between a sterilization device and an additional chamber module according to another embodiment.
Figure 17:
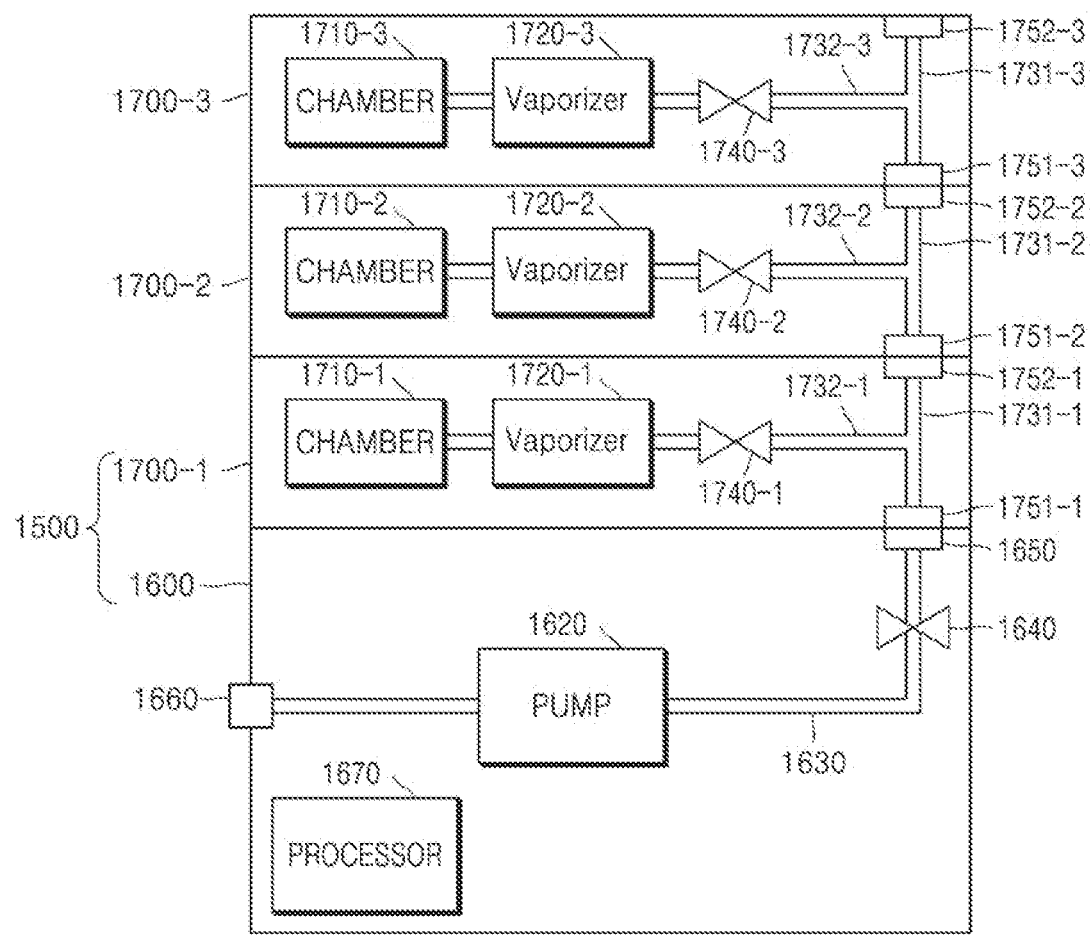
FIG. 17 is a block diagram of a detailed configuration of the sterilization device shown in FIG. 16.

FIG. 16 is a view showing a connection state between a sterilization device and an additional chamber module according to another embodiment. FIG. 17 is a block diagram of a detailed configuration of the sterilization device shown in FIG. 16.

Referring to FIGS. 16 and 17 together, a sterilization device 1500 includes a pump module 1600 and a basic chamber module 1700-1, and additional chamber modules 1700-2 and 1700-3 may be selectively connected to the sterilization device 1500.

According to an embodiment, the additional chamber modules 1700-2 and 1700-3 may be combined in a form that is sequentially stacked on top of the basic chamber module 1700-1.

The pump module 1600 and the basic chamber module 1700-1 of the sterilization device 1500 may be divided into mutually independent modules based on outer housings of the additional chamber modules 1700-2 and 1700-3.

Although FIGS. 16 and 17 illustrate a case in which two additional chamber modules 1700-2 and 1700-3 are connected to each other, the number of additional chamber modules that may be connected to each other is at least one.

Each of the basic chamber module 1700-1 and the additional chamber modules 1700-2 and 1700-3 may include chambers 1710-1 to 1710-3 receiving a target object, and vaporizers 1720-1 to 1720-3 connected to a chamber to supply a vaporized sterilant.

The pump module 1600 may include a pump 1620, an inner tube 1630, a valve 1640, a first combiner 1650, a filter 1660, and a processor 1670.

Except that each of the inner tube 1630 and the corresponding valve 1640 is composed of one, and a combiner is composed of one first combiner 1650, the remaining components 1620, 1660, and 1670 of the pump module 1600 are substantially the same as the pump module 1300A of FIGS. 2A and 2B or the pump module 1300B of FIGS. 3A and 3B.

The inner tube 1630 may connect the pump 1620 to the first combiner 1650 to allow internal air to flow.

The valve 1640 may be arranged in the inner tube 1630, and a flow of internal air flowing to the inner tube 1630 may be controlled by the valve 1640.

The first combiner 1650 of the pump module 1600 may be combined with a first combiner 1751-1 of the basic chamber module 1700-1.

According to an embodiment, the first combiner 1650 of the pump module 1600 may include a structure for physically combining and fixing the first combiner 1751-1 of the basic chamber module 1700-1.

According to an embodiment, the first combiner 1650 of the pump module 1600 and the first combiner 1751-1 of the basic chamber module 1701-1 may include a path structure therein such that the air inside may be circulated through a sealed path.

Because the additional chamber modules 1700-2 and 1700-3 have the same structure as the basic chamber module 1700-1, a detailed configuration will be described later below based on the structure of the basic chamber module 1700-1.

The basic chamber module 1700-1 may include a chamber 171-1, a vaporizer 170-1, inner tubes 171-1 and 1732-1, the first combiner 1751-1, and a second combiner 1752-1.

The first combiner 1751-1 of the basic chamber module 1701-1 is combined with the first combiner 1650 of the pump module 1600 to allow internal air to flow through the sealed path.

The second combiner 1752-1 of the basic chamber module 1700-1 is combined with the first combiner 1751 of the additional chamber modules 1700-2 to allow internal air to flow through the sealed path.

A first inner tube 1731-1 may be connected between the first combiner 1751-1 and the second combiner 1751-1 to allow internal air to flow therein.

The first inner tube 1731-1 may diverge into the second inner tube 1732-1 and connected to the chamber 1771-1 in order to circulate internal air between the chamber 1710-1 and the pump 1620.

A valve 1740-1 is on the second inner tube 1732-1, and the flow of internal air from the chamber 1710-1 may be controlled by the valve 1740-1.

According to an embodiment, as the basic chamber module 1700-1 and the additional chamber modules 1700-2 and 1700-3 are combined with the pump module 1600 in a stacked form, a communication path for exchanging data with the pump module 1600 may be electrically connected to the basic chamber module 1700-1 and the additional chamber modules 1700-2 and 1700-3 through a contact point. In this case, opening and closing of valves 1740-1 to 1740-3 of the chamber modules 1700-1 to 1700-3 may be controlled by the processor 1670 of the pump module 1600.

According to an embodiment, when one of the plurality of valves 1740-1 to 1740-3 (e.g., 1740-1) is controlled to be open, the processor 1670 may control the remaining valves (e.g., 1740-2 and 1740-3) to be closed. In this case, the processor 1670 may sequentially open the plurality of valves 1740-1 to 1740-3 according to a certain schedule to exhaust the corresponding chamber modules 1700-1 to 1700-3.

According to an embodiment, a processor 1770 may detect the number of connected one or more additional chamber modules (e.g., 1700-2 and 1700-3), and may control at least one of a pumping speed, a pumping intensity, and a pumping time of the pump 1620 depending on the number of detected additional chamber modules (e.g., 1700-2 and 1700-3). For example, as the number of detected additional chamber modules increases, the pumping speed may be increased, the pumping intensity may be increased, or the pumping time may be increased. For example, the processor 1770 may also detect the number of connected one or more additional chamber modules (e.g., 1700-2 and 1700-3) through a pressure change detected by the pump 1620.

In the above, embodiments have been described with reference to the accompanying drawings. However, the present disclosure is not limited thereto.

What is claimed is:

1. A sterilization pump assembly comprising:
   a pump module including a pump evacuating internal air of a chamber included in a first housing of a chamber module in which a target object is stored and a sterilization process of the target object is performed, in a second housing; and
a connector configured to connect the pump module to the chamber module so that the arrangement changes independently, and to move the internal air between the chamber module and the pump module,
wherein the pump module comprises a path through which the connector connected from the outside of the second housing of the pump module is connected to the inside of the second housing of the pump module to be connected to the pump.

2. The sterilization pump assembly of claim 1, wherein a connection point of the chamber module and the connector, a connection point of the pump module and the connector, and a length of the connector are fixed, and the arrangement changes by rotating the connector.

3. The sterilization pump assembly of claim 1, wherein a connection point of the chamber module and the connector and a connection point of the pump module and the connector are fixed, and the arrangement changes by rotating the connector or adjusting a length of the connector.

4. The sterilization pump assembly of claim 1, wherein a length of the connector is within 1.5 m.

5. The sterilization pump assembly of claim 1, further comprising:
a controller configured to control an operation of the pump using information related to a length of the connector measured through a user input or a pumping operation of the pump.

6. The sterilization pump assembly of claim 1, further comprising:
a controller configured to control the operation intensity or time of the pump,
wherein the controller determines suitability of the arrangement according to the connector through a test run mode in which the pump is operated with a reference value, or adjusts a value for controlling the pump in an operation mode other than the test run mode.

7. The sterilization pump assembly of claim 1, wherein the connector comprises a backflow prevention module to prevent the internal air from flowing into the chamber module.

8. The sterilization pump assembly of claim 1, wherein the connector is made of a flexible material, but comprises a material having chemical resistance inside a path through which the internal air flows, to prevent damage by a material included in the internal air.

9. The sterilization pump assembly of claim 8, wherein the connector comprises a hard material outside the path through which the internal air flows, to prevent damage or deformation due to external physical impact.

10. The sterilization pump assembly of claim 1, wherein the first housing further comprises a fan to discharge internal air of the first housing to the outside of the first housing.

11. A sterilization pump assembly comprising:
a chamber module including a chamber in which a sterilant is supplied to sterilize a target object stored therein and internal air is exhausted by a pump included in a first housing of a pump module, in a second housing; and
a connector configured to connect the chamber module to the pump module so that the arrangement changes independently, and to move the internal air between the chamber module and the pump module,
wherein the chamber module comprises a path through which the connector connected from the outside of the second housing of the chamber module is connected to the inside of the second housing of the chamber module to be connected to the chamber.

12. The sterilization pump assembly of claim 11, further comprising:
a filter arranged in a path for exhausting the internal air to the outside of the chamber module.

13. The sterilization pump assembly of claim 11, further comprising:
a sterilant container in which the sterilant is stored; and
a vaporizer configured to receive the sterilant from the sterilant container, heat the sterilant, vaporize the sterilant, and supply the sterilant to the chamber.

14. A sterilization system comprising:
a chamber module including a chamber in which a sterilant is supplied to sterilize a target object stored therein, in a first housing;
a pump module including a pump for exhausting internal air of the chamber in the chamber module, in a second housing; and
a connector configured to connect the chamber module to the pump module so that the arrangement changes independently, and to move the internal air between the chamber module and the pump module,
wherein the chamber module comprises a path through which the connector connected from the outside of the first housing of the chamber module is connected to the inside of the first housing of the chamber module to be connected to the chamber, and
the pump module comprises a path through which the connector connected from the outside of the second housing of the pump module is connected to the inside of the second housing of the pump module to be connected to the pump.

15. The sterilization system of claim 14, wherein the first housing has a chamber-connector combiner to which the connector is combined, and surrounds the outside of the chamber, and
the second housing has a pump-connector combiner to which the connector is combined, and surrounds the outside of the pump.

16. The sterilization system of claim 15, wherein the second housing further comprises a fan to exhaust air in the second housing to the outside.

17. The sterilization system of claim 14, further comprising:
a power unit configured to supply power to drive a pumping operation of the pump or a sterilization operation of the chamber; and
a power line configured to connect the power unit to the pump module and the chamber module so that the arrangement changes independently.

* * * * *